United States Patent
Brown

(10) Patent No.: US 10,264,828 B2
(45) Date of Patent: Apr. 23, 2019

(54) SENSORY MOTOR STIMULATION GARMENTS AND METHODS

(75) Inventor: Timothy W. Brown, Newport Beach, CA (US)

(73) Assignee: INTELLISKIN USA, LLC, Newport Beach, CA (US)

( * ) Notice: Subject to any disclaimer, the term of this patent is extended or adjusted under 35 U.S.C. 154(b) by 0 days.

(21) Appl. No.: 13/559,507

(22) Filed: Jul. 26, 2012

(65) Prior Publication Data

US 2013/0012853 A1 Jan. 10, 2013

Related U.S. Application Data

(63) Continuation-in-part of application No. 12/756,114, filed on Apr. 7, 2010, now Pat. No. 9,125,442, which is a continuation-in-part of application No. 12/551,420, filed on Aug. 31, 2009, now Pat. No. 9,119,707.

(Continued)

(51) Int. Cl.
| | |
|---|---|
| *A61G 15/00* | (2006.01) |
| *A41D 13/00* | (2006.01) |
| *A61F 5/02* | (2006.01) |
| *A41C 3/00* | (2006.01) |

(52) U.S. Cl.
CPC ........ *A41D 13/0015* (2013.01); *A41C 3/0057* (2013.01); *A61F 5/026* (2013.01)

(58) Field of Classification Search
CPC .. A61F 5/026; A61F 5/028; A61F 5/02; A61F 5/01; A61F 5/00; A41C 3/00; A41C 3/0057; A41C 3/005; A41C 3/0064; A41C 3/12; A41B 1/08; A41D 13/0015; A41D 13/0017; A41D 2400/38; A41D 13/0537;

(Continued)

(56) References Cited

U.S. PATENT DOCUMENTS

| | | |
|---|---|---|
| D43,765 S | 4/1913 | Lott |
| 1,129,515 A | 2/1915 | Perry |

(Continued)

FOREIGN PATENT DOCUMENTS

| | | |
|---|---|---|
| CA | 136013 | 3/1911 |
| DE | 202009013969 | 3/2010 |

(Continued)

OTHER PUBLICATIONS

Brown, Office Action, U.S. Appl. No. 12/551,420, dated Aug. 3, 2011, 16 pgs.

(Continued)

*Primary Examiner* — Victoria J Hicks

(74) *Attorney, Agent, or Firm* — Morgan, Lewis & Bockius LLP

(57) ABSTRACT

The disclosed garment includes a bra. The bra includes an anterior portion and a posterior portion, and the bra is fabricated from an elastomeric material. The garment also includes a spine band attached to the posterior portion of the bra and fabricated from an elastomeric material. The spine band extends longitudinally across the posterior portion of the bra from a neck region of the bra toward a waist portion of the bra. In use, the spine band is positioned over a spine of a wearer and stimulates cutaneous nerve receptors in a portion of a wearer's skin underneath the spine band.

19 Claims, 23 Drawing Sheets

Related U.S. Application Data

(60) Provisional application No. 61/534,815, filed on Sep. 14, 2011, provisional application No. 61/512,367, filed on Jul. 27, 2011.

(58) Field of Classification Search
CPC .............. A41D 13/1245; A41D 13/05; A41D 13/0512; A41D 2400/32; A41D 2600/10
USPC ...... 128/845, 874, 875, 846, 873, 869; 2/44, 2/45, 113; 450/2, 19, 64, 74, 8, 86, 76, 450/20, 75; 602/19, 60, 61
See application file for complete search history.

(56) References Cited

U.S. PATENT DOCUMENTS

| | | | |
|---|---|---|---|
| 1,483,635 A | 8/1921 | Horak | |
| 1,718,464 A | 3/1928 | Heyn | |
| 2,034,312 A | 3/1936 | Rubin | |
| 2,216,897 A | 10/1940 | Zoob | |
| 2,232,246 A | 2/1941 | Klein | |
| 2,456,190 A | 12/1948 | Heilbronner | |
| 2,477,792 A * | 8/1949 | Fratianni | A41C 1/06 2/44 |
| 2,591,462 A * | 4/1952 | Mungo | A41C 3/00 450/2 |
| 2,976,708 A | 3/1961 | Gordon | |
| 2,986,740 A | 6/1961 | Schudson | |
| 3,078,699 A | 2/1963 | Huntley | |
| 3,141,458 A | 7/1964 | Burbank | |
| 3,161,200 A | 12/1964 | Brickman | |
| 3,166,764 A | 1/1965 | Stedman et al. | |
| 3,292,616 A | 12/1966 | Freeman | |
| 3,663,797 A | 5/1972 | Marsh | |
| 3,683,910 A | 8/1972 | Mckenna | |
| 3,932,896 A | 1/1976 | Dottinger | |
| 3,934,583 A | 1/1976 | Hollingshead et al. | |
| 4,116,236 A | 9/1978 | Albert | |
| 4,261,060 A | 4/1981 | Zawacki | |
| D260,445 S | 9/1981 | Schreiber et al. | |
| D263,005 S | 2/1982 | Joseph | |
| 4,325,379 A | 4/1982 | Ozbey | |
| D264,516 S | 5/1982 | Joseph | |
| D269,220 S | 6/1983 | Joseph | |
| 4,474,573 A | 10/1984 | Detty | |
| 4,492,227 A | 1/1985 | Senn et al. | |
| 4,509,750 A | 4/1985 | Last | |
| 4,580,297 A | 4/1986 | Maejima | |
| 4,625,336 A | 12/1986 | Derderian | |
| 4,670,913 A | 6/1987 | Morell et al. | |
| 4,698,847 A | 10/1987 | Yoshihara | |
| D297,581 S | 9/1988 | Wirth | |
| 4,832,010 A | 5/1989 | Lehman | |
| 4,862,523 A | 9/1989 | Lipor | |
| D306,230 S | 2/1990 | Nigro | |
| 4,920,769 A | 5/1990 | Rickeri | |
| 5,040,245 A | 8/1991 | Staley | |
| 5,109,546 A | 5/1992 | Dicker | |
| 5,131,100 A | 7/1992 | Atwater et al. | |
| 5,154,690 A | 10/1992 | Shiono | |
| 5,201,074 A | 4/1993 | Dicker | |
| 5,263,923 A | 11/1993 | Fujimoto | |
| 5,306,229 A | 4/1994 | Brandt et al. | |
| 5,328,447 A | 7/1994 | Kapounek et al. | |
| 5,344,384 A | 9/1994 | Ostrow et al. | |
| 5,367,708 A | 11/1994 | Fujimoto | |
| 5,555,566 A | 9/1996 | Kuhn | |
| 5,662,512 A | 9/1997 | Cohen | |
| 5,742,936 A | 4/1998 | Tronc | |
| D394,135 S | 5/1998 | Gunnerson | |
| 5,820,575 A | 10/1998 | Cabrera et al. | |
| 5,823,851 A * | 10/1998 | Dicker | A41C 3/0057 2/73 |
| 5,823,981 A | 10/1998 | Grim et al. | |
| 5,857,990 A | 1/1999 | Maas | |
| 5,873,768 A * | 2/1999 | Fleischman-Ament | A41C 3/0057 2/73 |
| 5,937,442 A | 8/1999 | Yamaguchi et al. | |
| D413,424 S | 9/1999 | Davies et al. | |
| 6,047,406 A | 4/2000 | Dicker et al. | |
| 6,176,816 B1 | 1/2001 | Dicker et al. | |
| 6,243,879 B1 | 6/2001 | Lyden | |
| 6,306,111 B1 | 10/2001 | Dean | |
| D457,709 S | 5/2002 | Davis | |
| 6,440,094 B1 * | 8/2002 | Maas | A61F 5/3738 2/44 |
| D462,154 S | 9/2002 | Fairhurst et al. | |
| 6,464,656 B1 | 10/2002 | Salviucci et al. | |
| 6,728,973 B1 | 5/2004 | Webley et al. | |
| 6,892,396 B2 | 5/2005 | Uno et al. | |
| 6,936,021 B1 | 8/2005 | Smith | |
| 6,945,945 B2 | 9/2005 | Givler et al. | |
| D517,777 S | 3/2006 | Thunstedt | |
| 7,037,281 B1 | 5/2006 | Jeffrey et al. | |
| 7,037,284 B2 | 5/2006 | Lee | |
| 7,041,074 B1 | 5/2006 | Averianov et al. | |
| D525,412 S | 7/2006 | O'Mahony | |
| 7,134,969 B2 | 11/2006 | Citron et al. | |
| D564,182 S | 3/2008 | Wiens | |
| 7,415,734 B2 | 8/2008 | Donnelly | |
| D584,881 S | 1/2009 | Curran | |
| 7,516,498 B2 | 4/2009 | Toffy | |
| 7,568,966 B2 * | 8/2009 | Abbey | A41C 3/0057 2/268 |
| D601,326 S | 10/2009 | DiFrancesco | |
| D619,783 S | 7/2010 | Jones et al. | |
| 7,841,369 B1 | 11/2010 | Osborne | |
| D628,770 S | 12/2010 | Kanada et al. | |
| D628,771 S | 12/2010 | Kanada et al. | |
| 7,861,319 B1 | 1/2011 | Torry | |
| 7,871,388 B2 | 1/2011 | Brown | |
| D632,050 S | 2/2011 | Zarabi | |
| D641,129 S | 7/2011 | Zarabi | |
| D641,130 S | 7/2011 | Zarabi | |
| D641,133 S | 7/2011 | Zarabi | |
| D654,659 S | 2/2012 | Scott-Curran | |
| D654,660 S | 2/2012 | Jones et al. | |
| D657,532 S | 4/2012 | Gaeir et al. | |
| D658,352 S | 5/2012 | Pinner | |
| D666,384 S | 9/2012 | Schindler | |
| D668,837 S | 10/2012 | Palladino | |
| 8,281,412 B2 | 10/2012 | Byrnes | |
| D674,168 S | 1/2013 | Kajino et al. | |
| D683,525 S | 6/2013 | Lamartino | |
| D690,906 S | 10/2013 | Lambertz | |
| D691,347 S | 10/2013 | Lambertz | |
| D696,488 S | 12/2013 | Kenney et al. | |
| D697,696 S | 1/2014 | Obrecht et al. | |
| D698,127 S | 1/2014 | Cheatham | |
| 8,707,463 B2 | 4/2014 | Orloff | |
| D704,455 S | 5/2014 | Blakely | |
| D709,668 S | 7/2014 | Martz | |
| D714,522 S | 10/2014 | Boyer et al. | |
| D718,917 S | 12/2014 | Stampley | |
| D720,119 S | 12/2014 | Pankhurst et al. | |
| D731,749 S | 6/2015 | Waldman | |
| D732,270 S | 6/2015 | Murphy | |
| D732,271 S | 6/2015 | Fischer | |
| D733,393 S | 7/2015 | Callahan | |
| D733,996 S | 7/2015 | Brown | |
| D734,916 S | 7/2015 | Turner | |
| D737,543 S | 9/2015 | Turner | |
| D745,249 S | 12/2015 | Aitch | |
| D745,250 S | 12/2015 | McClain | |
| D747,843 S | 1/2016 | Gallo | |
| D755,473 S | 5/2016 | Darmour | |
| D758,045 S | 6/2016 | Suarez | |
| D761,518 S | 7/2016 | Martz | |
| D763,548 S | 8/2016 | Harmande | |
| D764,142 S | 8/2016 | Gallo et al. | |
| D765,344 S | 9/2016 | McArthur et al. | |
| D765,427 S | 9/2016 | Blakely et al. | |
| D765,947 S | 9/2016 | McManus | |

(56) References Cited

U.S. PATENT DOCUMENTS

| | | | |
|---|---|---|---|
| D766,599 S | 9/2016 | Blakely et al. | |
| D769,582 S | 10/2016 | McArthur et al. | |
| D770,130 S | 11/2016 | Lomax | |
| D770,142 S | 11/2016 | McArthur et al. | |
| D771,905 S | 11/2016 | McArthur et al. | |
| D780,406 S | 3/2017 | Brown | |
| D790,158 S | 6/2017 | McArthur et al. | |
| 2002/0143373 A1 | 10/2002 | Courtnage et al. | |
| 2004/0016041 A1 | 1/2004 | Uno et al. | |
| 2005/0112976 A1 | 5/2005 | McMurrey et al. | |
| 2005/0193461 A1 | 9/2005 | Caillibotte et al. | |
| 2005/0197607 A1 | 9/2005 | Brown | |
| 2005/0240134 A1 | 10/2005 | Brown | |
| 2006/0000478 A1 | 1/2006 | Taylor | |
| 2006/0026740 A1 | 2/2006 | Vargas et al. | |
| 2006/0253960 A1 | 11/2006 | Horn et al. | |
| 2007/0111868 A1 | 5/2007 | Fujii et al. | |
| 2007/0214541 A1 | 9/2007 | Kawasaki et al. | |
| 2007/0294801 A1 | 12/2007 | Furgerson et al. | |
| 2008/0060113 A1 | 3/2008 | Walsh | |
| 2008/0194178 A1* | 8/2008 | Smith | A41C 3/0064 450/8 |
| 2008/0208089 A1 | 8/2008 | Newkirk et al. | |
| 2008/0256675 A1 | 10/2008 | Di Lorenzo | |
| 2008/0295216 A1 | 12/2008 | Nordstrom et al. | |
| 2008/0295230 A1 | 12/2008 | Wright et al. | |
| 2009/0062704 A1 | 3/2009 | Brown et al. | |
| 2009/0133181 A1 | 5/2009 | Nordstrom et al. | |
| 2009/0270012 A1 | 10/2009 | Melarti et al. | |
| 2009/0320180 A1 | 12/2009 | Torry | |
| 2010/0010568 A1 | 1/2010 | Brown | |
| 2010/0050313 A1 | 3/2010 | Shackelford, Jr. | |
| 2010/0088803 A1 | 4/2010 | Orloff | |
| 2010/0242151 A1 | 9/2010 | Mather | |
| 2010/0251454 A1 | 10/2010 | Kiernan | |
| 2010/0256717 A1 | 10/2010 | Brown | |
| 2010/0299799 A1 | 12/2010 | Belluye et al. | |
| 2011/0083246 A1 | 4/2011 | Vitarana | |
| 2011/0131697 A1 | 6/2011 | Kawahara | |
| 2011/0213283 A1 | 9/2011 | Brown | |
| 2011/0271415 A1 | 11/2011 | Torry | |
| 2012/0078147 A1 | 3/2012 | Ogulnick et al. | |
| 2013/0012853 A1 | 1/2013 | Brown | |
| 2013/0211302 A1 | 8/2013 | Brown | |
| 2013/0253397 A1 | 9/2013 | Samoodi | |
| 2013/0326785 A1 | 12/2013 | Cornacchiari et al. | |
| 2014/0196190 A1 | 7/2014 | Brown | |
| 2015/0237926 A1 | 8/2015 | Placanica et al. | |

FOREIGN PATENT DOCUMENTS

| | | |
|---|---|---|
| EP | 1891868 A1 | 2/2008 |
| EP | 2505089 A2 | 10/2012 |
| GB | 4035319 | 5/2014 |
| JP | 2002-302810 A | 10/2002 |
| JP | 2004-100116 A | 4/2004 |
| JP | 2012-031564 A | 2/2012 |
| JP | D1460836 | 2/2013 |
| WO | WO 2005/086752 A2 | 9/2005 |
| WO | WO 2005/086840 A2 | 9/2005 |
| WO | WO 2008/002432 A2 | 1/2008 |
| WO | WO 2008/093105 A1 | 8/2008 |
| WO | WO 2011/025675 A1 | 3/2011 |
| WO | WO 2013/016670 A1 | 1/2013 |

OTHER PUBLICATIONS

Brown, Office Action, U.S. Appl. No. 12/551,420, dated Mar. 15, 2012, 18 pgs.
Brown, Office Action, U.S. Appl. No. 12/756,114, dated Dec. 19, 2012, 23 pgs.
Intelliskin LLC, ISR and Written Opinion, PCT/US2010/048648, dated Oct. 11, 2012, 10 pgs.
Intelliskin USA LLC, Communication pursuant to Article 94(3) EPC, EP 10745106.4, dated Jan. 14, 2013, 5 pgs.
Brown, Interview Summary, U.S. Appl. No. 12/126,338, dated Jan. 31, 2014, 3pgs.
Brown, Office Action, U.S. Appl. No. 12/126,338, dated Jun. 11, 2013, 17pgs.
Brown, Final Office Action, U.S. Appl. No. 12/126,338, dated Feb. 15, 2011, 18 pgs.
Brown, Office Action, U.S. Appl. No. 12/126,338, dated Jun. 9, 2010, 14 pgs.
Brown, Office Action, U.S. Appl. No. 13/831,228, dated Apr. 4, 2014, 5 pgs.
Intelliskin USA LLC, Notification of the First Office Action, JP 2012-526827, dated Mar. 13, 2014, 4 pgs.
Brown, Office Action, U.S. Appl. No. 12/551,420, dated Sep. 30, 2013, 25 pgs.
Brown, Office Action, U.S. Appl. No. 12/756,114, dated Jul. 18, 2013, 23 pgs.
Intelliskin USA LLC, Communication under Rule 71(3) EPC Intention to Grant, EP 10745106.4, dated Oct. 17, 2013, 6 pgs.
Intelliskin USA LLC, International Search Report and Written Opinion, PCT/US2010/045427, dated Nov. 25, 2010, 10 pgs.
Brown, Office Action, U.S. Appl. No. 12/551,420, dated May 28, 2014, 12 pgs.
Intelliskin USA LLC, International Preliminary Report on Patentability, PCT/US2010/048648, dated Jan. 28, 2014, 6 pgs.
Brown, Notice of Allowance, U.S. Appl. No. 29/546,091, dated Jul. 1, 2016, 7 pgs.
Intelliskin USA LLC, Official Notce of Preliminary Rejection, KR30-2016-0009956, dated Jun. 8, 2016, 3 pgs.
Intelliskin USA LLC, Certificate of Grant, AU2010286851, dated Dec. 17, 2015, 1 pg.
Intelliskin USA LLC, Decision to Grant a Patent, CN201280046850.4, dated Feb. 24, 2016, 5 pgs.
Intelliskin USA LLC, Letters Patent, CN201280046850.4, dated Jun. 8, 2016, 3 pgs.
Isportscloth:Eastbas Men's Evapor L/S Baseball Compression Top Boy's Grade School 6-shirt, Announced Jun. 18, 2014, [Site Visited Jun. 23, 2016] http://www.isportscloth.com/2014/06/eastbay-mens-evapor-is-baseball-compression-to-boys-grade-school-t-shrt/, xx pgs.
Nike-Dri-Fit-Knit-Long-Sleeve-Womens-Running-Shirt, Announced Feb. 15, 2013 [Site Visited Jun. 23, 2016], http://www.smustyle.com/on-a-nike-note/nike-dri-fit-knit-long-sleave-womens-running-shirt-520294_734_a/. Xx pgs.
PULSE Activewear Delivers Merino Performance, Announced May 26, 2014 [Site Visited Jun. 23, 2014], http://www.feedthehabit.com/outdoors/pulde-activewear-merino-review/, xx pgs.
"Actively Yours. http://www.activelyyours.com/Merchant2/merchant.mvc?page=AY/PROD/cycling/lsland_Jersey. Dec. 2010. ""HIND Island Cycling Jersey Short Sleeve"", 1 pg."
Brown, Final Office Action, U.S. Appl. No. 29/449,312, dated May 28, 2015, 7 pgs.
Bizzieliving. http://www.bizzieliving.com/improve-your-posture-while-you-excercise/. Dec. 2011. Intelliskin Shirt, 3 pgs.
DHGate. http://www.dhgate.com/product!sports-compression-running-fitness-excercise/164726955.html. Date Unknown: Viewed May 2015. "sports compression running Fitness Excercise cycling short sleeve Clothing shirt", 11 pgs.
DailyStoke. http://www.dailystoke.com/gear-categories/intelliskin-gear-review-good-enuf-for-kelly-slater-good-enuf-for-you/. Nov. 29, 2011. "lntelliskin shirt", 4 pgs.
DailyPilot. http://!articles.dailypilot.com/2012-01-09/news/tn-dpt-0110-brown-20120109_1_bad-posture-perfect-posture-products. Jan. 2012, Intelliskin Shirt, 1 pg.
GearPatrol. http:I/gearpatrol.com/2011/07/07/intelliskin-foundation-shirt-2-0/, Jul. 7, 2011. "Intelliskin Foundation Shirt 2.0", 2 pgs.
News & Views. http:1/news.health.com/2011/05/24/can-toning-clothing-really-help-you-lose- weight/. May 2011, Intelliskin Eve Shirt, 1 pg.
Intelliskin USA LLC, Communication Pursuant Article 94(3), EP14723932.1, dated Nov. 11, 2016 3 pgs.
Intelliskin USA LLC, Certificate of Design Registration, AU201615076, dated Nov. 21, 2016, 7 pgs.

(56) References Cited

OTHER PUBLICATIONS

Intelliskin USA LLC, Notification of Rectification, CN201630466549.X, dated Nov. 18, 2016, 2 pgs.
Intelliskin USA LLC, Notice of Allownce and Notification of Grant, CN201630059222.0, dated Oct. 10, 2016 4 pgs.
Intelliskin USA LLC, Certificate of Grant, EM003372986-0001, dated Sep. 9, 2016, 5 pgs.
Intelliskin USA LLC, Certificate of Grant, EM003372986-0002, dated Sep. 9, 2016, 5 pgs.
Intelliskin USA LLC, Intention to Grant a Patent, EP14188899.0, dated Nov. 9, 2016, 53 pgs.
Brown, Notice of Allowance, U.S. Appl. No. 12/551,420, dated Jun. 22, 2015, 11 pgs.
Brown, Notice of Allowance, U.S. Appl. No. 12/756,114, dated Jun. 30, 2015, 9 pgs.
Brown, Office Action, U.S. Appl. No. 14/214,356, dated Jul. 14, 2015, 13 pgs.
Brown, Notice of Allowance, U.S. Appl. No. 29/449,312, dated Sep. 10, 2015, 7 pgs.
Eckler's Corvette, http://www.ecklerscorvette.com/corvette-contrast-t-shirt-short-sleeve-women-s-white-with-black-and-yellow-side-panels.html, Oct. 2011, "Corvette Contrast T-Shirt, short Sleeve, Women's, White With Blac, & Yellow Side Panels".
Eil.com, http://eil.com/shop/moreinfo.asp?catalogid=400605, Date Unknown, Viewed Sep. 2015, "Guns n Roses Gn'F'nR's Football Shirt".
Intelliskin USA LLC, International Report on Patentability, PCT/US2014/029690, dated Sep. 15, 2015, 6 pgs.
Intelliskin USA LLC, Communication Pursuant to Article 94(3) EPC, EP12751174.9, dated Nov. 19, 2014, 4 pgs.
Intelliskin USA LLC, Communication Pursuant to Article 94(3) EPC, EP12751174.9, dated Jul. 27, 2015, 4 pgs.
Intelliskin USA LLC, Certificate of Grant, HK13100261-7, dated Aug. 21, 2015, 3 pgs.
Intelliskin USA LLC, Notification of 2nd Office Action, CN201280046854, dated Aug. 27, 2015, 29 pgs.
Rakuten Global Market, http:/global.rakuten.com/en/store/t-on/item/ton-62264451/, Customer Review from Mar. 2015, Nike Golf Shirt.
Intelliskin USA LLC, Extended European Search Report, EP14188899.0, dated Mar. 11, 2015, 5 pgs.
Intelliskin USA LLC, Office Action, CA 2.772.296 dated Aug. 24, 2016, 4 pgs.
Intelliskin USA LLC, Notice of Reasons for Rejection, JP 2014-230764, dated Aug. 3, 2016, 4 pgs.
Intelliskin USA LLC, Communication Pursuant to Article 94(3) EPC, EP12751174.9, dated May 12, 2016, 3 pgs.
Intelliskin USA LLC, Notification of the Office Action, JP 2013/017534, dated May 30, 2014, 4 pgs.
Intelliskin USA LLC, Notification of the Office Action, JP 2014/003694, dated Sep. 12, 2014, 3 pgs.
Intelliskin USA LLC, Decision to Grant, EP10745106.4, dated Oct. 2, 2014, 3 pgs.
Intelliskin USA LLC, Patent Examination Report, AU2010286851, dated Aug. 21, 2014, 3 pgs.
Brown, Final Office Action, U.S. Appl. No. 14/214,356, dated Aug. 2, 2016, 13 pgs.
Brown, Final Office Action, U.S. Appl. No. 13/831,228, dated Feb. 13, 2015, 6 pgs.
Intelliskin USA LLC, International Search Report and Written Opinion, PCT/US2014/029690, dated Jul. 18, 2014, 9 pgs.
Intelliskin USA LLC, Decision to Grant, JP 2012-526827, dated Oct. 20, 2014, 5 pgs.
Intelliskin USA LLC, Certificate of Patent, JP 2012-526827, dated Dec. 10, 2014, 3 pgs.
Intelliskin USA LLC, Decision of Registration, JP2013-017534, dated Aug. 28, 2014, 2 pgs.
Intelliskin USA LLC, Certificate of Registration, JP2013-017534, dated Nov. 12, 2014, 3 pgs.
Intelliskin USA LLC, Certificate of Grant, EP10745106.4, dated Oct. 29, 2014, 3 pgs.
Intelliskin USA LLC, Notification of the First OA, CN201280046850.4, dated Dec. 24, 2014, 13 pgs.
Brown, Notice of Allowance, U.S. Appl. No. 29/538,491, dated Dec. 28, 2016, 8 pgs.
Intelliskin USA LLC, Official Notice, HK1601739-6, dated Nov. 21, 2016, 2 pgs.
Intelliskin USA LLC, Intention to Grant, EP12751174.9, dated Nov. 29, 2016, 73 pgs.
Intelliskin USA LLC, Examiner's Report, CA170455, dated Dec. 13, 2016, 2 pgs.
Intelliskin USA LLC, Notice of Registration Decision, KR2016-0009956, dated Nov. 22, 2016, 4 pgs.
Intelliskin USA LLC, Notice of Registration Decision, KR2016-0043868, dated Nov. 21, 2016, 4 pgs.
Intelliskin USA LLC, Notice of Registration Decision, KR2016-0043869, dated Dec. 1, 2016, 4 pgs.
Intelliskin USA LLC, Notice of Registration Decision, KR2016-0043870, dated Nov. 21, 2016, 4 pgs.
Intelliskin USA LLC, Notice of Registration Decision, KR2016-0043871, dated Jan. 2, 2017, 4 pgs.
Intelliskin USA LLC, Notice of Registration Decision, KR2016-0043872, dated Nov. 21, 2016, 4 pgs.
Brown, Office Action, U.S. Appl. No. 29/557,614, dated Oct. 5, 2017, 5 pgs.
Intelliskin USA LLC, Certificate of Patent, CA2,772,296, dated Dec. 18, 2017, 1 pg.
Intelliskin USA LLC, Certificate of Registration, CA170455, dated Oct. 16, 2017, 1 pg.
Intelliskin USA LLC, Certificate of Registration, JP 2016-019620, dated Jun. 16, 2017, 2 pgs.
Intelliskin. Notice of Registration Decision, KR30-2016-0044484, dated Aug. 9, 2017, 3 pgs.
Intelliskin. Certificate of Registration, KR30-2016-0044484, dated Sep. 4, 2017, 2 pgs.
Intelliskin USA LLC, Certificate of Grant, EP12751174.9, dated Oct. 18, 2017, 1 pg.
Intelliskin USA LLC, Rejection Decision, CN201630466549.X, dated Sep. 11, 2017, 5 pgs.
Brown, Final Office Action, U.S. Appl. No. 14/214,356, dated May 1, 2017, 16 pgs.
Intelliskin USA LLC, Certificate of Registration, HK1601739-6, dated Mar. 17, 2017, 10 pgs.
Intelliskin USA LLC, Notice of Allowance, CA2.772.296, dated May 2, 2017, 1 pg.
Intelliskin USA LLC, Decision to Grant, JP 2014-230764, dated Mar. 22, 2017, 4 pgs.
Intelliskin USA LLC, Certificate of Patent, JP 2014-230764, dated Apr. 28, 2017, 4 pgs.
Intelliskin USA LLC, Decision to Grant, JP 2016-019620, dated May 16, 2017, 5 pgs.
Intelliskin USA LLC, Official Notice of Preliminary Rejection, KR30-2016-0044484, dated Jan. 20, 2017, 4 pgs.
Intelliskin. Official Notice of Preliminary Rejection, KR30-2016-0044484, dated May 31, 2017, 3 pgs.
Intelliskin USA LLC, Communication Under Rule 71(3), Intention to Grant, EP12751174.9, dated May 2, 2017, 68 pgs.
Intelliskin USA LLC, Patent Examination Report, AU2015264849, dated Sep. 15, 2016, 2 pgs.
Intelliskin USA LLC, 2nd Office Action, CN201630466549.X, dated May 16, 2017, 2 pgs.
Intelliskin USA LLC, Certificate of Grant, EP14188899.0, dated Apr. 19, 2017, 1 pg.

\* cited by examiner

SENSORY MOTOR STIMULATION GARMENTS AND METHODS

RELATED APPLICATIONS

This application claims the benefit under 35 U.S.C. 119(e) of the filing dates of each of U.S. Provisional Application No. 61/512,367, filed Jul. 27, 2011, and U.S. Provisional Application No. 61/534,815, filed Sep. 14, 2011, and this application is a continuation-in-part of U.S. application Ser. No. 12/756,114, filed Apr. 7, 2010, which is a continuation-in-part of U.S. application Ser. No. 12/551,420, filed on Aug. 31, 2009. All of these applications are incorporated by reference herein in their entirety.

FIELD OF THE INVENTION

The present invention relates generally to body mechanics and, more particularly, to posture improvement garments configured to be worn on a user's upper body and that promote sensory motor system stimulation.

BACKGROUND

The importance of good posture is well known among health professionals. Posture generally refers to the alignment of the body and, more specifically, to the relative static and dynamic positioning of the body and its limbs. Ideally, in a body exhibiting good posture, the spine has no lateral curvature and the legs have little angulation in the knees and ankles. In addition, when viewed from the side, the spine forms a slight S-shape with the two curves of the S-shape being evenly disposed on opposite sides of an imaginary line extending downwardly from the head through the body's center. Such an alignment provides an even distribution of body weight over the spine and lower body joints resulting in a relatively uniform distribution of pressure on the intervertebral discs of the spine.

The effects of poor posture are well documented and include limited range of motion wherein muscles, such as the pectoral muscles in the chest, may be permanently shortened due to a hunched-over upper body position. Other effects of poor posture include discomfort in the form of headaches at the base of the skull and pain in the shoulders, arms, and hands. Additionally, poor posture may lead to pain in the jaw due to a forward-head position, as well as decreased lung capacity due to decreased volume of the chest cavity and lungs. One of the most common consequences of poor posture is the onset of lower back pain which may increase with advancing age. Finally, a hunched-over upper body position of poor posture can add years to one's appearance. Many attempts to improve posture involve the use of straps. For example, see U.S. patent application Ser. No. 10/795,656, filed on Mar. 8, 2004, the entirety of which is incorporated by reference herein.

However, by assuming good posture, gravitational forces may be more evenly distributed through the bones, ligaments and muscles of the body. Maintaining good posture is equally important during passive (static) activities such as sitting and standing, as well as during dynamic activities such as walking, running, and lifting. Theoretically, the slight S-shape of the spine that is characteristic of good posture should preferably be maintained during both static and dynamic activities. Unfortunately, our increasingly sedentary lifestyle, wherein many hours are spent sitting in front of a computer, driving an automobile, or watching television, has an adverse effect on posture. Such static activities may result in forward protrusion of the head and neck, rounding of the thoracic and lumbar spine and stretching of the spinal ligaments. Such stretching gradually causes pain in the neck and upper back and results in fatiguing of the body's muscles and ligaments. Poor posture during dynamic activities such as running and lifting results in inefficient body movements with increased stress on muscles and ligaments.

Maintaining an awareness of proper posture during static and dynamic activities may sometimes prevent overstressing of muscles and ligaments. In addition, maintaining an awareness of proper posture may train certain muscles through muscle memory such that proper posture eventually becomes a habit. However, it is sometimes difficult to maintain an awareness of proper posture during mentally challenging activities such as working at a computer, or during physically challenging activities such as participating in aggressive sports. Physical therapists may utilize postural therapy to improve the posture of a patient. Such postural therapy may include techniques such as shoulder taping and breathing exercises. Conventional chiropractic techniques may utilize body manipulation and treatment to help keep the patient's spine in alignment. However, the patient must take the time and energy to visit the offices of a physical therapist or a chiropractor in order to receive the needed postural therapy and/or chiropractic manipulation. Moreover, alternative treatment, such as cutaneous nerve stimulation, is often overlooked as a method to improve the patient's posture.

In a preferred embodiment, the present invention is adapted to continuously train and develop certain body muscles and therefore optimal movement patterns, such that the user's static and dynamic posture may be improved. In addition, the present invention preferably allows for developing such muscle training during static activities such as standing and sitting. In addition, the present invention preferably discretely allows for developing such muscle training during dynamic activities such as walking, running and during other daily activities. Furthermore, the present invention preferably helps improve the user's posture and musculature such that it is progressively adjusted in accordance with changes or improvements in the user's posture or musculature over time. Finally, the present invention preferably helps improve and adjust the user's posture according to varying physiological parameters between users including differences in user's age, body size, muscular development and underlying pathophysiologic status.

SUMMARY

The invention is a posture improvement or sensory motor stimulation device that is adapted to provide neuromuscular stimulation or proprioceptive therapy using a combination of gripping of the skin, pressure, torque and angle simultaneously applied to the user in order to train body muscles for proper posture through muscle memory. The device comprises a garment designed to be worn by a user and which is adapted to envelop at least a portion of the user's torso and, in at least one embodiment, at least a portion of the user's upper arms. This garment is preferably configured like a short-sleeved undershirt or T-shirt. However, it can also be configured like a tank top, long sleeve shirt, sleeveless shirt, etc. The garment is often referred to herein generically as a shirt. It will be understood that this covers all embodiments of the garment that are worn on the user's torso.

Pressure is applied to the user's skin in order to apply specific pressure to the skin to stimulate the cutaneous nerve receptors, thereby resulting in enhanced proprioception and enabling the wearer to self correct body alignment and posture. Mechanoreceptors are sensitive to pressure, stretch, torque on muscles, tendons, joint lining, etc. These are the receptors that help the wearer to adjust and adapt. The nociceptor is also stimulated by the design of the garment and reacts by decreasing neurotransmitter frequency and causes an instant decrease in pain. This is done preferably by configuring the garment as a relatively tight, form-fitting shirt. The garment is adapted to envelop at least a portion of the user's torso and at least a portion of the user's upper arms. The garment has an inner and an outer surface, a front side, a back side, opposing lateral sides, and a pair of partial sleeves. The front side includes a chest portion and a stomach portion, while the back side includes a back portion. The garment also defines opposing shoulder portions and a waist portion extending about a lower end of the garment. A short-sleeved version of the garment allows for effective training of the user's pectoralis major muscles located in the user's chest. In addition, the short-sleeved configuration of the garment enhances the user's range of motion, particularly at the shoulder joints, in addition to providing conditioning of the user's rotator cuffs. This short sleeved version allows for effective retraining of the overused and understretched pectoralis minor and major, serratus, subscapularis muscles. It three dimensionally balances muscles of the chest, neck, under arms, upper back and inter scapula. It also simultaneously aligns the spine and joints of the upper extremities allowing for improved range of motion, optimized biomechanics and improves overall function and recovery.

The garment may be fabricated from a stretchable, yet taut material in order to provide the desirable form-fitting feature such that specific pressure may be readily applied to the surface of the skin over specific anatomical landmarks for neuromuscular stimulation. In this regard, the garment is preferably fabricated from elastomeric material that is also preferably breathable and/or which has moisture wicking capabilities such as may be provided by a material comprised of a combination of LYCRA® and spandex, FABRI-FOAM®, nylon or the like.

More particularly, there is provided a garment for sensory motor stimulation/retraining of the wearer, which comprises an anterior portion and a posterior portion joined to the anterior portion. Each of the anterior portion and the posterior portion are fabricated from a thin, elastomeric material which is form-fitting, in order to apply pressure to the surface of the wearer's skin to enhance neuromuscular stimulation thereto. A panel for stimulating the wearer's proprioception is integrated with the posterior garment portion and positioned to extend over the upper back or inter scapular region of the wearer. The panel for stimulating the wearer's proprioception is fabricated from an elastomeric material and having characteristics which cause the garment to stimulate optimal scapular position. In one embodiment, the panel for stimulating the wearer's proprioception is comprised of the same elastomeric material as the posterior portion. In an alternative embodiment, the panel for stimulating the wearer's proprioception is comprised of a heavier, denser elastomeric material than that comprising a remainder of the posterior portion.

In some embodiments of the present invention, the inventive garment further comprises an elastic band disposed on the panel for stimulating the wearer's proprioception. This elastic band is fabricated from a stronger elastomeric material than that comprising the panel for stimulating the wearer's proprioception, and is positioned to substantially coincide with the inferior medial border of the wearer's scapula.

In a presently preferred embodiment of the present invention, the panel for stimulating the wearer's proprioception is positioned to extend along substantially an entire length of the spine of the wearer.

The inventive garment preferably further comprises at least one and preferably a plurality of shoulder strap portions positioned to extend from the panel upwardly and over the wearer's shoulder toward the garment anterior portion. The shoulder strap portion is integrated with the garment posterior portion and is comprised of elastomeric material.

In one embodiment, the panel for stimulating the wearer's proprioception is generally triangular in shape, positioned to extend downwardly from the shoulders of the wearer toward an apex positioned to be disposed at approximately the small of the wearer's back.

Preferred embodiments of the invention further comprise at least one and preferably a plurality of arm strap portions extending from the panel for stimulating the wearer's proprioception and positioned to proceed about an arm of the wearer toward the anterior portion of the garment. The arm strap portions are integrated with the garment posterior portion and are comprised of elastomeric material. Nerve receptor stimulators are preferably disposed on an inner surface of the garment, for contacting the wearer's skin and creating additional proprioceptive stimulation when the garment is worn. These nerve receptor stimulators preferably comprise a plurality of strategically placed neuro nubs, comprising soft, tacky bumps and extending inwardly from the inner surface of the garment. Alternatively, the nerve receptor stimulators may comprise viscoelastic pads for stimulating the wearer's proprioception.

In preferred embodiments, the material comprising each of the anterior and posterior portions also comprises a moisture wicking material. The panel for stimulating the wearer's proprioception is stitched to the posterior portion, though it may also be joined by alternative methods as well. One possibility is to integrate the panel into the posterior portion of the garment by blending it into the base material forming the posterior portion, using advanced production techniques, forming a single, seamless, composite layer.

In another aspect of the invention, there is disclosed a method of making a garment for proprioceptively treating a wearer. This method comprises a step of joining a posterior portion to an anterior portion of the garment together, wherein each of the posterior portion and the anterior portion are comprised of a thin, elastomeric material, so that the joined posterior and anterior portions form a garment resembling a shirt. The method further comprises a step of joining a panel for stimulating the user's proprioception, comprised of an elastomeric material, to the posterior portion, in a location wherein when the garment is worn by a user, the panel for stimulating the user's proprioception is disposed over at least a portion of the user's spine and inter scapular region. These steps may be performed in interchangeably, as they are not sequence dependent. In one presently preferred embodiment, the joining steps are performed by stitching the posterior portion and the anterior portion together, and stitching the panel to the posterior portion. In some embodiments, the panel for stimulating the user's proprioception comprises a second layer of material over the base material forming the posterior portion. In other embodiments, the panel for stimulating the user's proprioception is integrated with the posterior portion in such a manner that only a single layer of material results.

The shirt creates a sensation/cue on the skin through the design that specifically bends, compresses and directs the nerve receptors in the skin (peripheral nervous system with nerve endings on skin, in or connected to muscles, tendons, joint lining, etc.; these regions may include, or be connected to, 20-80 nerve endings/square inch) to be pulled in such a way and in such a specific direction that tells the brain to instantly relax and lengthen specific, over used, under stretched muscles while the brain simultaneously commands the opposite (front to back and/or side to side), weak, under toned, under supportive muscles to contract, tone and support the wearer's core and torso. This natural reflexive response is known as reciprocal inhibition and this naturally balancing muscle stimulation system retrains the wearer's muscles every time the garment is put on to create a wearable, therapeutic short/pant that decreases muscle and joint pain, improves recovery from training, travel and injury and improves aberrant biomechanics that create muscle imbalances that are the major cause of most musculoskeletal injuries today. In a preferred embodiment, the desired cues and responses are provided by straps or bands that twist the wearer's body, tissues or muscles in a spiral manner. Spirals and spiral physiology are naturally occurring within the human body and nature as a whole, and can all be related through the Fibonacci numbers or Fibonacci structure. The Fibonacci numbers are nature's numbering system. They appear everywhere in nature, from the leaf arrangement in plants, to the pattern of the florets of a flower, the bracts of a pinecone, or the scales of a pineapple. The Fibonacci numbers are therefore applicable to the growth of every living thing, including a single cell, a grain of wheat, a hive of bees, and even humans.

The Fibonacci sequence is 1, 1, 2, 3, 5, 8, 13, 21, 34, 55, and so on. It begins with the number 1, and each new term from there is the sum of the previous two. The limit ratio between the terms is 0.618034 . . . , an irrational number variously called the "Golden Ratio" and/or the "divine proportion," but in this century more succinctly "PHI" ($\phi$) after the architect Phidias, who designed the Parthenon. In other words, any two adjoining numbers equal the next higher number. For example, 5+8=13. Any number divided by the next higher number gives a ratio of 0.618. For example, 8/13=0.618. Any number divided by the next lower number gives a reciprocal of 1.618.

In the lower numbers the ratios are not exact, but close enough for practical purposes. Both the Fibonacci sequence and the Golden Ratio appear in natural forms ranging from the geometry of the DNA molecule (and the human body) to the physiology of plants and animals. In recent years, science has taken a quantum leap in knowledge concerning the universal appearance and fundamental importance of Fibonacci mathematics. Some of history's greatest minds, from Pythagoras to Isaac Newton, have held phi ($\phi$) and the Fibonacci sequence in the highest esteem and reverence.

All human senses, including hearing, touch, taste, vision and pain receptors, have not only spiral physiology, but also response curves that are logarithmic (having a Fibonacci structure). Cellular action membrane potentials, which are important for muscles and the nervous system, have a voltage equal to the log of the ratio of the ion concentration outside the cell to that of inside the cell. The brain and nervous systems are made from the same type of cellular building units and look similar microscopically, so the response curve of the central nervous system is probably also logarithmic. This spiral/helical physiology is utilized by the design of the garment of the present invention. The straps extend about the axis of the wearer's torso.

The design stimulates the sensory motor system (sensori includes the nervous system combined with the (motor) musculoskeletal system), instantly cueing a wearer's upper body into muscular balance and ideal anatomical alignment. This stimulates the user's anatomy on both a conscious and subconscious level. This instantly allows the wearer to move with more biomechanical efficiency which means using less energy while enhancing and optimizing body mechanics. This has an effect that decreases normal wear and tear on joints and enhances healthy circulation and recovery from training, travel, and injury.

It will be appreciated that virtually every time a user puts the garment on, he/she is training The garment makes weak muscles work. When a weak muscle works it helps to balance the muscles so the body is using all sides to work with rhythm and synchrony making the body move with more efficiency, greater fluidity and less effort. The garment supports and protects the joint structures by enhancing the body's dynamic restraint system.

Another embodiment of the invention, where the sensory motor system stimulation features are positioned on the inside of the garment. This embodiment is preferably a fusion of the latest technical fabrics and space age materials combined with the most recent scientific research in functional human physiology, fitness and performance, anatomy and the sensory motor system. The garment or shirt preferably increases sensory motor stimulation to muscles that are commonly found to be imbalanced and dysfunctional and interfaces with the human sensory motor system. In use, the shirt enhances the constant feed forward, feedback system so the wearer's body can more effectively both consciously and subconsciously, adapt to the proprioceptive information provided to the sensory motor system when the shirt is worn. The inside of the shirt is lined with special thermo elastic plastic or rubber bands or straps that contact the cutaneous nerve receptors in the skin with specifically designed angles, lengths and densities that apply different pressures and directional pull. This embodiment also helps decrease shirt migration that occurs with wearers who are very active in the shirts.

In a preferred embodiment, bands or straps can be placed in the following areas of the shirt:
1. Transverse abdominus stimulation and support, which is crucial for full function core strength.
2. Internal abdominal oblique stimulation and support, which is important for core stability and function.
3. Thoracic extension stimulation and support, which begins at the first thoracic vertebra and interlocks each vertebral segment down to T12 and preferably provides a spring back effect because the spinal erector muscles are cued/stimulated to contract when the wearer lets his/her head and spine slump forward. In other words, the elastic material in the garment that is positioned over the thoracic spine prevents the normal stretch of the skin when the head drops forward. This is what stimulates the cutaneous nerve receptors to cause the muscles to respond appropriately.
4. Lower rectus abdominus stimulation and support. The bands that compress and stimulate lower abdominal tone and support the lumbosacral spine and core, adding tone to the lower abs while simultaneously decreasing hip flexor tone (dominance) and hyper lordosis (pot belly and butt out) that are common in society today.

5. Flexible lumbar mobility support, which provides compression and proprioceptive stimulation to enhance natural support and stability of the lumbar spine.
6. Interscapular area of shirt uses horizontal bars (may be slightly curved or angled to fit natural anatomy or based on the Fibonacci pattern) that can be increased or decreased in size, elasticity and density (depending on the wearer or desired effects) to provide the most desirable level of interscapular support depending on posture fitness, injury, health objectives, etc.
7. Also lining the inside of the shirt in a preferred embodiment, are neuro nub sensors or neuro nubs that are placed in specific and very richly innervated acupuncture meridian points. The neuro nubs bend and massage these points every time the wearer moves a muscle (adjacent to the nubs). This increases circulation and what Chinese medicine refers to as CHI or life energy directly to these areas that are commonly found to be out of balance and have restricted or congested chi.

This embodiment of the shirt is designed to stretch and open where the muscles most commonly are tight and over used while simultaneously sending cues to under used, under toned muscles to contract, tone and add support. The shirt is preferably manufactured in a seamless style that better conforms to the intimate curves and shapes of the body making the shirt comfortable whether the wearer is training, competing or recovering in it. Over time, just as the body adapts to negative information (like sitting at a computer and slumping), it will adapt and remodel to new, "positive" information.

In accordance with one preferred embodiment of the present invention, there is provided a garment adapted to be worn by a wearer that includes an outer layer configured to be worn over at least a portion of the wearer's torso. The outer layer has an anterior portion, a posterior portion, an inner surface and an outer surface. The garment also includes at least one sensory motor stimulation member affixed to the inside surface of the outer layer. When the garment is worn by a wearer the at least one sensory motor stimulation member contacts a portion of the wearer's skin and when the wearer moves the at least one sensory motor stimulation member alters the normal stretch of the portion of the skin contacted by the at least one sensory motor stimulation member, thereby stimulating the wearer's cutaneous nerve receptors to cause the wearer's muscles to respond appropriately.

In accordance with another preferred embodiment of the present invention, there is provided a garment for stimulation of a wearer's sensory motor system. The garment includes a main body portion that includes an anterior portion and a posterior portion and at least one sensory motor stimulation member associated with the main body portion. The garment is configured to be worn over at least a portion of the wearer's torso and is form-fitting when worn by the wearer. The at least one sensory motor stimulation member contacts a portion of the wearer's skin when the garment is worn and is fabricated from an elastomeric material that causes the garment to stimulate the cutaneous nerve receptors in the portion of the wearer's skin contacted by the at least one sensory motor stimulation member. In a preferred embodiment, the at least one sensory motor stimulation member includes at least one of a shoulder strap, upper arm strap, serratus strap, diamond shaped plate, lower abdominal band, thoracic vertebra patch, scapular band and lumbar spine band. In another preferred embodiment, the main body portion defines a generally vertically extending axis and the at least one sensory motor stimulation member is positioned such that it extends in a spiral about the axis of the main body portion.

In accordance with another preferred embodiment of the present invention, there is provided a method that includes donning a garment that covers at least a portion of the wearer's torso and moving while wearing the garment. The garment includes a main body portion, and at least one form-fitting sensory motor stimulation member associated with the main body portion. The at least one sensory motor stimulation member contacts a portion of the wearer's skin. The method also includes stimulating the cutaneous nerve receptors in the portion of the wearer's skin contacted by the at least one sensory motor stimulation member. In a preferred embodiment, the method also includes the step of removing and donning the garment a plurality of times over a period of time. At the end of the period of time the muscles positioned under the at least one sensory motor stimulation member are in a more optimal position than at the beginning of the period of time. Optimal means that there is a balance between agonist and antagonist muscles as they support human structure versus the common effects of gravity. In other words, what a person of ordinary skill in the art would consider perfect posture.

In accordance with yet another preferred embodiment of the present invention, there is provided a device adapted to be worn by a wearer. The device includes a main body portion configured to be worn over at least a portion of the wearer's torso and means, associated with the main body portion, for stimulating a plurality of the wearer's cutaneous nerve receptors when the wearer moves its torso when wearing the device. The main body portion includes an anterior portion, a posterior portion, an inner surface and an outer surface. In a preferred embodiment, when the device is worn by the wearer and the wearer moves, the means for stimulating a plurality of the wearer's cutaneous nerve receptors alters the normal stretch of the portion of the skin contacted by the means for stimulating a plurality of the wearer's cutaneous nerve receptors.

In accordance with some embodiments, a garment for stimulation of a wearer's sensory motor system includes a form-fitting shirt. The form-fitting shirt has an anterior portion and a posterior portion, and the shirt is fabricated from an elastomeric material. The garment also includes a spine band attached to the posterior portion of the shirt and also fabricated from an elastomeric material. The spine band extends longitudinally across the posterior portion of the shirt from a neck region of the shirt toward a waist portion of the shirt. When in use, the spine band stimulates cutaneous nerve receptors in a portion of a wearer's skin underneath the spine band.

In accordance with some embodiments, a garment for stimulation of a wearer's sensory motor system includes a form-fitting shirt. The form-fitting shirt has an anterior portion and a posterior portion, and the shirt is fabricated from an elastomeric material. The garment also includes a spine band attached to the posterior portion of the shirt and also fabricated from an elastomeric material. The spine band extends longitudinally across the posterior portion of the shirt from a neck region of the shirt toward a waist portion of the shirt. When in use, the spine band stimulates cutaneous nerve receptors in a portion of a wearer's skin underneath the spine band. The garment also includes at least one additional band attached to the shirt. The at least one additional band is fabricated from a third elastomeric material different from the first and second elastomeric material. When in use, the at least one additional band stimulates cutaneous nerve receptors in one or more portions of a wearer's skin underneath the at least one additional band. The at least one additional band includes four or more shoulder bands. Each shoulder band radiates from the spine band and extends over a respective shoulder region of the shirt toward the anterior portion of the shirt. The four or more shoulder bands include at least two inner shoulder bands and at least two outer shoulder bands. The at least two inner shoulder bands are positioned between the at least two outer shoulder bands. The at least one additional band also includes two or more oblique bands. Each oblique band extends around a respective side of the shirt from the posterior portion of the shirt toward the waist portion and the anterior portion of the shirt. Two shoulder bands and two oblique bands form two sets of bands, and each set includes a shoulder band and an oblique band positioned in a helical pattern about a longitudinal axis formed through a center of the shirt. The at least one additional band also includes serratus bands. Each serratus band extends around a respective side of the shirt from the posterior portion of the shirt to the anterior portion of the shirt. The serratus bands include a plurality of fingers pointing toward opposite sides of the waist portion of the shirt. The at least one additional band includes rotator cuff bands. Each rotator cuff band extends from the posterior portion of the shirt over a respective upper arm portion of the shirt toward the anterior portion of the shirt. The at least one additional band also includes at least one lower abdominal band positioned on the anterior portion toward the waist portion of the shirt. The at least one additional band also includes pectoral anchor bands extending from the neck region on the anterior portion of the shirt toward a chest portion of the anterior portion of the shirt, such that the shoulder bands are each connected at one end to the spine band and at the opposite end to the respective pectoral anchor band. Furthermore, the garment is configured to allow natural motion of the wearer, while providing a viscoelastic resistance in a longitudinal direction along the at least one additional band. In addition, the at least one additional band is attached to the shirt, such that in use, the at least one additional band applies a corrective force along a longitudinal direction of the at least one additional band when the wearer is in a neutral posture, for training body muscles for proper posture through muscle memory.

In accordance with some embodiments, a method of stimulating a wearer's sensory motor system includes donning a garment that covers at least a portion of a wearer's torso. The garment includes a form-fitting shirt. The form-fitting shirt has an anterior portion and a posterior portion, and the shirt is fabricated from an elastomeric material. The garment also includes a spine band attached to the posterior portion of the shirt and also fabricated from an elastomeric material. The spine band extends longitudinally across the posterior portion of the shirt from a neck region of the shirt toward a waist portion of the shirt. The garment further more includes at least one additional band attached to the shirt and also fabricated from an elastomeric material. The method also includes moving while wearing the garment, and stimulating the cutaneous nerve receptors in one or more portions of a wearer's skin underneath the at least one additional band by providing force along a longitudinal direction of the at least one additional band.

In accordance with some embodiments, a garment includes a first garment portion defining an inner surface, an outer surface, and two armholes. The inner surface is configured to contact a wearer. The garment also includes one or more pads attached to the first garment portion adjacent to each armhole.

In accordance with some embodiments, a garment includes a first garment portion defining an inner surface and an outer surface, the inner surface being configured to contact a wearer. The garment also includes an inner layer attached to the inner surface of the first garment portion.

In accordance with some embodiments, a method for making a garment includes providing a first garment portion that defines an inner surface and an outer surface. The method also includes applying plastisol on the inner surface of the first garment portion in accordance with a predefine shape.

In accordance with some embodiments, a garment includes a bra that includes an anterior portion and a posterior portion. The bra is fabricated from an elastomeric material. The garment also includes a spine band attached to the posterior portion of the bra and fabricated from an elastomeric material. The spine band extends longitudinally across the posterior portion of the bra from a neck region of the bra toward a waist portion of the bra, such that in use, the spine band is positioned over a spine of a wearer and stimulates cutaneous nerve receptors in a portion of a wearer's skin underneath the spine band.

In accordance with some embodiments, a garment for stimulation of a wearer's sensory motor system includes a bra that includes an anterior portion and a posterior portion. The bra is fabricated from a first elastomeric material and defining an inner surface. The garment also includes a spine band attached to the posterior portion of the bra and fabricated from a second elastomeric material different from the first elastomeric material. The spine band extends longitudinally across the posterior portion of the bra from a neck region of the bra toward a waist portion of the bra, such that in use, the spine band is positioned over a spine of a wearer and stimulates cutaneous nerve receptors in a portion of a wearer's skin underneath the spine band. The garment includes at least one additional band attached to the bra and fabricated from the first or second elastomeric material, such that in use, the at least one additional band stimulates cutaneous nerve receptors in one or more portions of a wearer's skin underneath the at least one additional band. The at least one additional band includes four or more shoulder bands, each radiating from the spine band and extending over a respective shoulder region of the bra toward the anterior portion of the bra. The four or more shoulder bands include at least two inner shoulder bands and at least two outer shoulder bands, and the at least two inner shoulder bands are positioned between the at least two outer shoulder bands. The garment is configured to allow natural motion of the wearer, while providing a viscoelastic resistance in a longitudinal direction along the at least one additional band. The at least one additional band is attached to the bra and configured, such that in use, the at least one additional band applies a corrective force along a longitudinal direction of the at least one additional band when the wearer is in a neutral posture, for training body muscles for proper posture through muscle memory.

In accordance with some embodiments, a method of stimulating a wearer's sensory motor system includes donning a garment that covers at least a portion of a wearer's torso. The garment includes a bra that includes an anterior portion and a posterior portion. The bra is fabricated from an elastomeric material. The garment also includes a spine band attached to the posterior portion of the bra and fabricated from an elastomeric material. The spine band extends longitudinally across the posterior portion of the bra from a neck region of the bra toward a waist portion of the bra along a region that is, in use, positioned over a spine of a wearer.

At least one additional band attached to the bra and fabricated from an elastomeric material. The method includes moving while wearing the garment, and stimulating the cutaneous nerve receptors in one or more portions of a wearer's skin underneath the at least one additional band by providing force along a longitudinal direction of the at least one additional band.

The invention, together with additional features and advantages thereof, may be best understood by reference to the following description taken in conjunction with the accompanying illustrative drawings. In these accompanying drawings, like reference numerals designate like parts throughout the figures.

BRIEF DESCRIPTION OF THE DRAWINGS

Like numerals refer to like structures or features throughout the several views of the drawings.

DETAILED DESCRIPTION OF PREFERRED EMBODIMENTS

Figure 1:
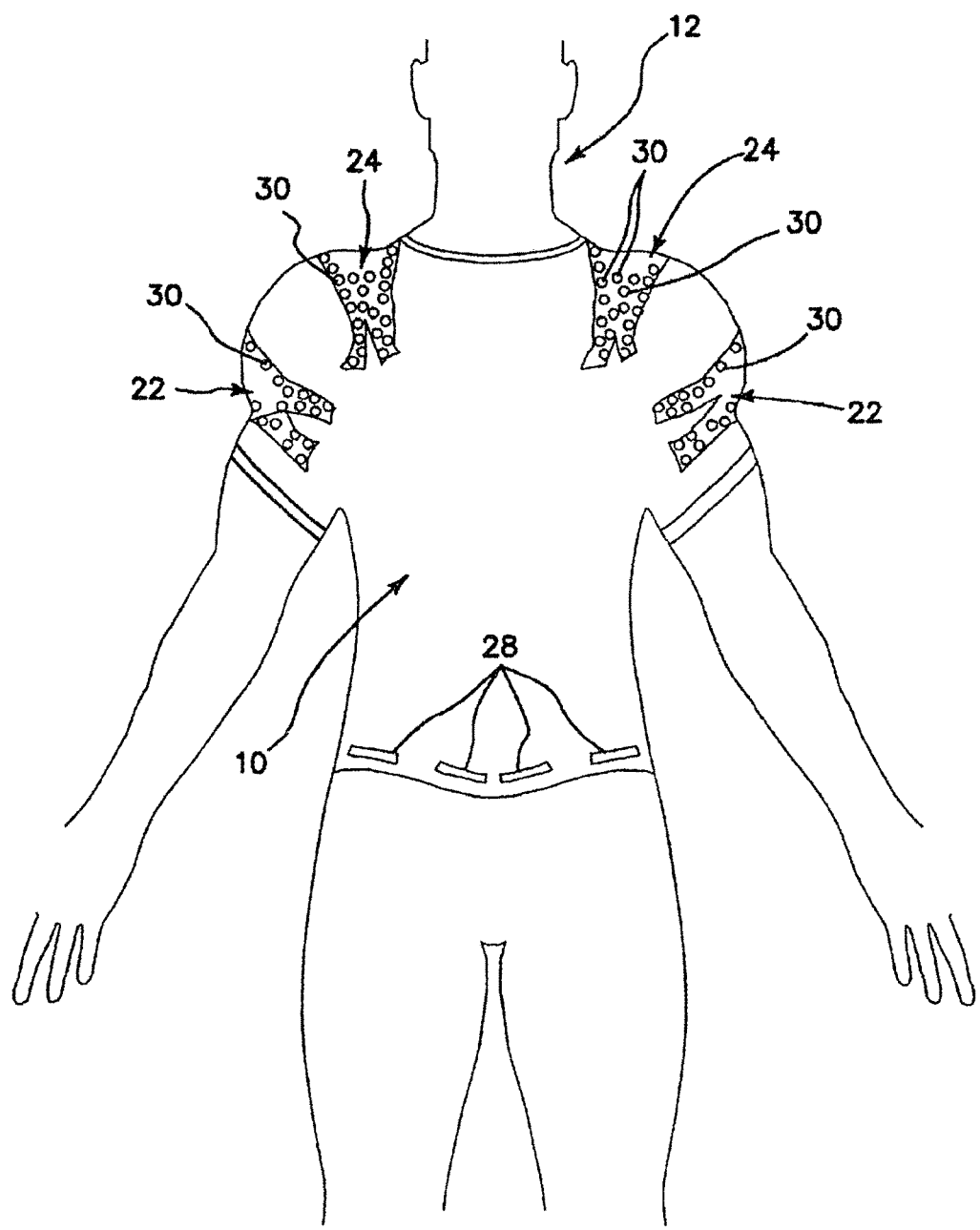
FIG. 1 is an anterior view of an embodiment of the garment of the present invention, being worn by a user.

As shown in the drawings, for purposes of illustration, preferred embodiments of posture improvement garments are shown and described. It will be appreciated that terms such as "front," "back," "top," "bottom," "side," "short," "long," "up," "down," and "below" used herein are merely for ease of description and refer to the orientation of the components as shown in the figures. It should be understood that any orientation of the garments and the components thereof described herein is within the scope of the present invention.

Figures 2, 2A:
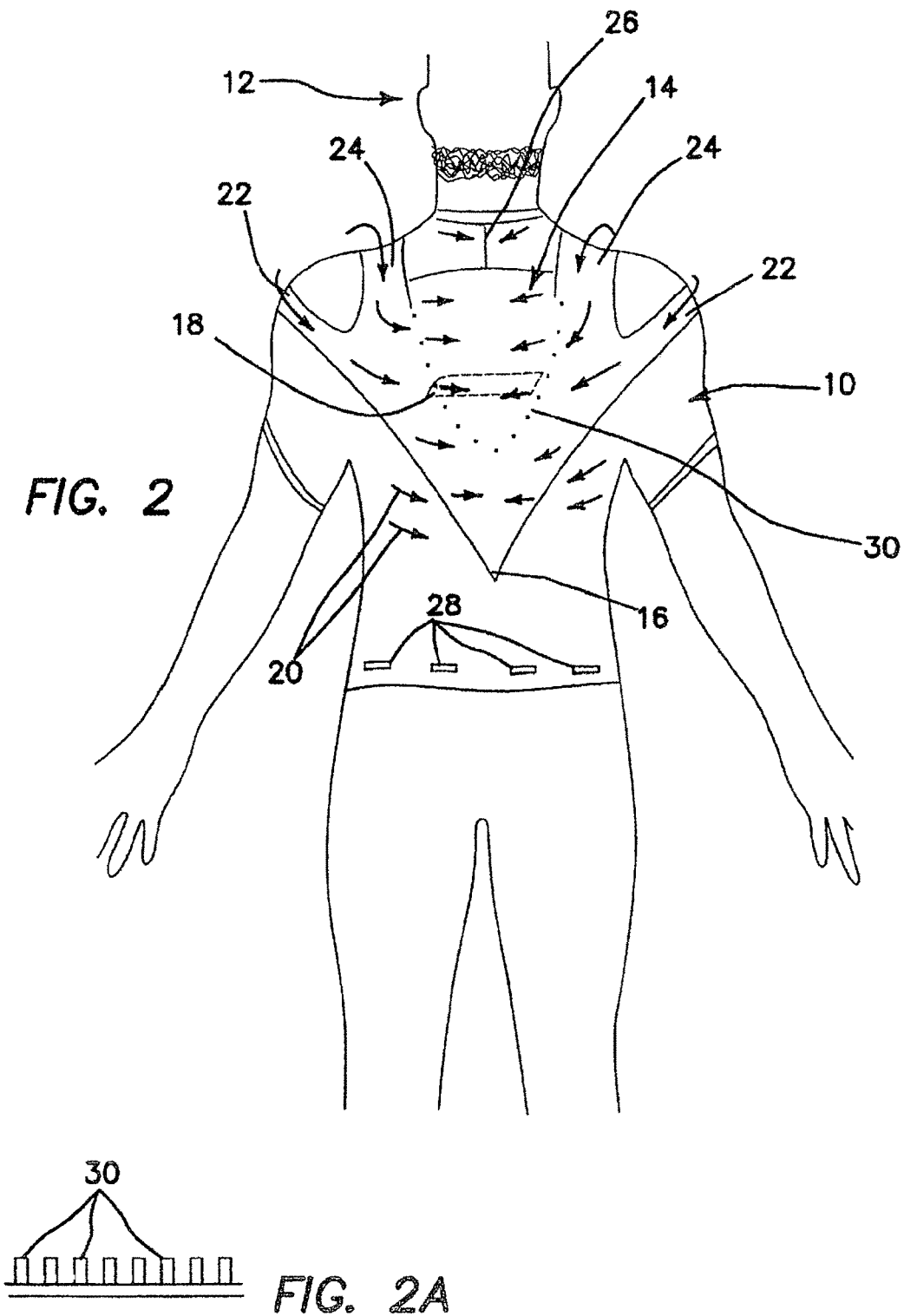
FIG. 2 is a posterior view of the garment of FIG. 1.
FIG. 2A is a side view of a section of neuro nubs for use with the garments of the invention.

Referring now to the drawings, wherein the showings are for purposes of illustrating the present invention and not for purposes of limiting the same, FIGS. 1 and 2 are views of a first embodiment of a posture improvement garment 10, which is configured to be worn by a user 12 and which is configured to envelop at least a portion of the user's torso and at least a portion of the user's upper arms. In this regard, the garment 10 is generally configured to be similar to one of a short-sleeved undershirt, T-shirt, or polo shirt. While the illustrated garment 10 is designed as a "pull-over" style, the garment may also be provided with an open or partially open front or back portion, which is selectively closeable by means of known garment closure systems, such as a zipper, buttons, snaps, and the like. Such a style eases the wearability of the garment because it can be put on or removed without pulling the garment over one's head.

The embodiments illustrated in the aforementioned '656 application have been shown to have a remarkable proprioceptive therapeutic effect on the wearer, substantially improving his/her posture and relieving pain related to poor posture and related muscle strain. However, the illustrated embodiments in that application are not particularly adapted for use in casual recreational and social settings, or for routine retail sale to consumers. Because of the external strapping, if they are to be worn in such settings, aesthetics dictate that they be worn under external garments, which must be relatively bulky and heavy to adequately cover the therapeutic garment. Accordingly, the present invention performs many of the same functions as the prior embodiments disclosed in the '656 application without the use of external strapping. Similar proprioceptive effects are achieved by the use of strategically placed stretch panels and pads for stimulating the wearer's proprioception, integrated directly into the material used to fabricate the garment. As a result, the garments of the present invention are particularly suited for the consumer market, as they are attractive and comfortable.

Regarding material from which the garment 10 may be fabricated, it is preferred that the material be thin, and have an elastic quality that stretches or moves with the user's body, in order to provide a desirable form-fitting feature such that pressure may be readily applied to the surface of the user's skin in order to enhance neuromuscular stimulation thereto. The material may contain, but not be limited to, polyester, spandex, elastic, nylon, and the like. It may have metal ions woven into it, or other mechanical sweat wicking, temperature regulating materials which are known in the art and function in an equivalent way to regulate temperature and wick moisture. Its breathability and/or moisture wicking capabilities function to improve the user's comfort level during periodic wearing of the device 10.

Referring particularly to FIG. 2, there is shown an elastic stretch panel or posture patch 14 for stimulating the user's proprioception. As shown, the patch 14 is generally triangular in shape (its border is represented by the dotted outline in the drawing), and is welded or sewn into the upper back, or inter scapular region, extending downwardly from both shoulders of the user 12 to a point 16 disposed at the small of the user's back. The posture patch 14 for stimulating the user's proprioception is fabricated from an elastic material, which may be the same as that from which the garment 10 is fabricated, or it may alternatively be a heavier, denser elastic material to assist in support of relatively weak middle or lower trapezious, rhomboids major and minor, and serratus musculature respectively. The purpose of the patch 14 is to stimulate optimal scapular position and spinal alignment. This is the functional base for optimal posture and scapular kinematics. The patch may be disposed as a second layer atop the base layer of the garment, or may alternatively be blended (integrated) into the garment material, using suitable production techniques, to form a single composite layer.

In a preferred embodiment, an elastic band 18 is employed in about the midpoint of the patch 14, which is fabricated from stronger elastic than that used for the patch 14. The band 18 is positioned to substantially coincide with the inferior medial border of the scapula.

As demonstrated by the arrows 20, the base layer of the garment 10 has a posterior (retracting) directional influence on the body of the user 12.

Referring now to FIG. 1, as well as FIG. 2, two upper arm straps 22 and two shoulder straps 24 begin on the anterior side of the garment 10 (FIG. 1) and continue around to the posterior side, as shown (FIG. 2). These straps 22, 24 are built into the garment 10, in much the same way as the patch 14. The arm straps 22 are designed to provide a specific directional pull on the infraspinatus and teres minor muscles. The shoulder straps 24 are designed to influence problems relating to posterior scapular tilt, in part by influencing the pectoralis minor muscle adjacent to the coracoid process.

Darts 26 (FIG. 2) may be used to enhance posterior pull/cue to help the scapula to attain an optimal position.

As can be seen in each of FIGS. 1 and 2, viscoelastic tape 28 may be disposed about the hem of the garment 10, for the purpose of preventing migration of the garment. Alternative means providing a tacky surface for contacting the user's skin may instead be used.

It should be noted that the specific angles of arrows shown in FIG. 2 may indicate coupled motion influence upon the axis of the scapula, caused by the various elastomeric elements of the garment 10.

The various dots 30 shown in FIGS. 1 and 2 are neuro nubs. These neuro nubs are more particularly shown in FIG. 2A. These neuro nubs 30 preferably comprise soft, tacky bumps, or cutaneous nerve receptor stimulators, which are designed to provide a massaging, stimulating effect when the user moves. As shown, these nubs 30 are disposed on each of the straps 22 and 24, where they stimulate portions of the body adjacent to rotator cuff muscle attachment points on the humerus, as well as pectoralis minor muscles in the vicinity of the coracoid process. In general, the inventor has found that patterns of such neuro nubs 30 are helpful in creating proprioceptive stimulation, and also function to provide decreased migration of the garment 10 as the body moves throughout its full range of motion. They are disposed at specific areas on the inside surface of the garment, to stimulate cutaneous nerve receptors in the skin and soft tissue structures to enhance "noise" that creates cues to the brain, enhancing muscle balance, body position awareness, posture, function, and performance.

Desired locations of the neuro nubs 30 are at known acupuncture sites, as stimulation of these specific energy meridians enhances blood flow and stimulates normal physiology to organs and soft tissues that supply movement, support, and information crucial to those seeking optimal health and function.

Although one elastic panel 18 and four elastic straps 22, 24 are shown in the embodiment of FIGS. 1 and 2, a plurality of such panels 18 and/or straps 22, 24, of various shapes and sizes, may be employed if desired. As noted, the stretch panels 18 and straps 22, 24 may be constructed of the same or similar materials as the garment 10 or patch 14. Alternatively, the stretch panels 18 and/or straps 22, 24 are constructed of an elastomeric material different from the material for the garment 10 or patch 14. The panels 18 and straps 22, 24 function to stimulate muscles that are too tight (the panels/straps will stretch these muscles), or too loose and undertoned (the panels/straps will add tone to these muscles and encourage/stimulate them to work). Conventional approaches to date have focused on mechanical support systems that have been shown to create atrophy and a reliance on a brace, which in the long term can create a system of dependence that the inventor believes is detrimental to optimal health and efficient recovery and performance. The elastic or stretch panels/straps as well as the patch(es) 14, on the other hand, create specific traction and tactile stimulation of cutaneous nerves in the skin. There are a minimum of 20,000 of such nerves per square inch of skin that will transfer specific information to the receptors (mechanoreceptors/nociceptors) that exist by the thousands/ millions in the muscle, tendon, ligament, and joint surfaces, causing a predictable unloading of specific, predictable and common muscle imbalances that create and perpetuate joint stress and injury throughout the body.

Figure 3:
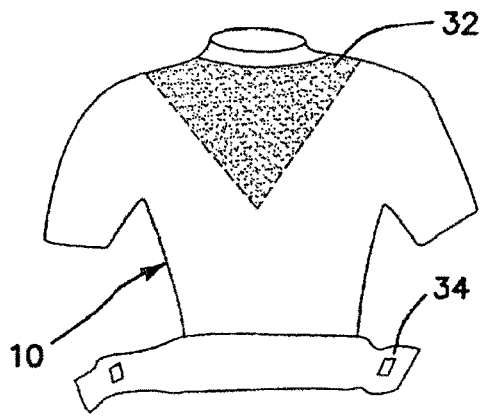
FIGS. 3-5 are sequential views of another embodiment of a garment of the present invention, illustrating a sequence of fabrication of the garment to include the advantageous posture-improving features of the invention.
Figure 4:
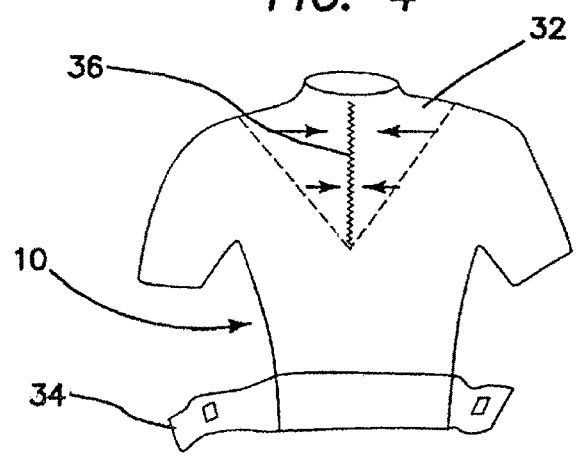
Figure 5:
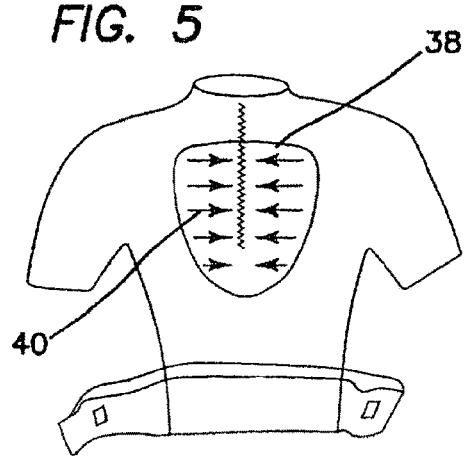
Figure 6:
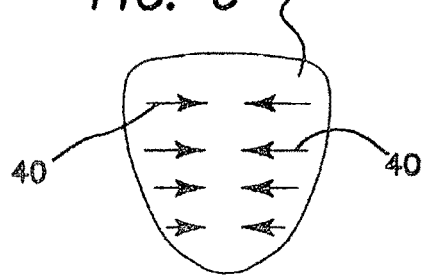
FIG. 6 is a view, in isolation, of a specific tension elastic posture patch for use in fabricating the garment of FIGS. 3-5.

Now referring to FIGS. 3-6, there is shown a somewhat modified embodiment of the garment 10 of the invention. The posterior side of the garment is shown. The views in FIGS. 3-5 are sequential, wherein, as shown in FIG. 3, a V 32 has been cut out of the shirt. In this embodiment of the invention, an optional belt or strap 34 is provided at the base of the garment 10. As shown in FIG. 4, the edges of the V 32 have been sewn together along seam 36. Then for additional support, an elastic posture patch 38 is applied over the seam 36 as shown. The elastic patch 38 is adapted to apply specific tension along arrows 40 to assist the user's posture, as discussed above.

Figure 7:
FIG. 7 is an anterior view of still another embodiment of a garment of the present invention.
Figure 8:
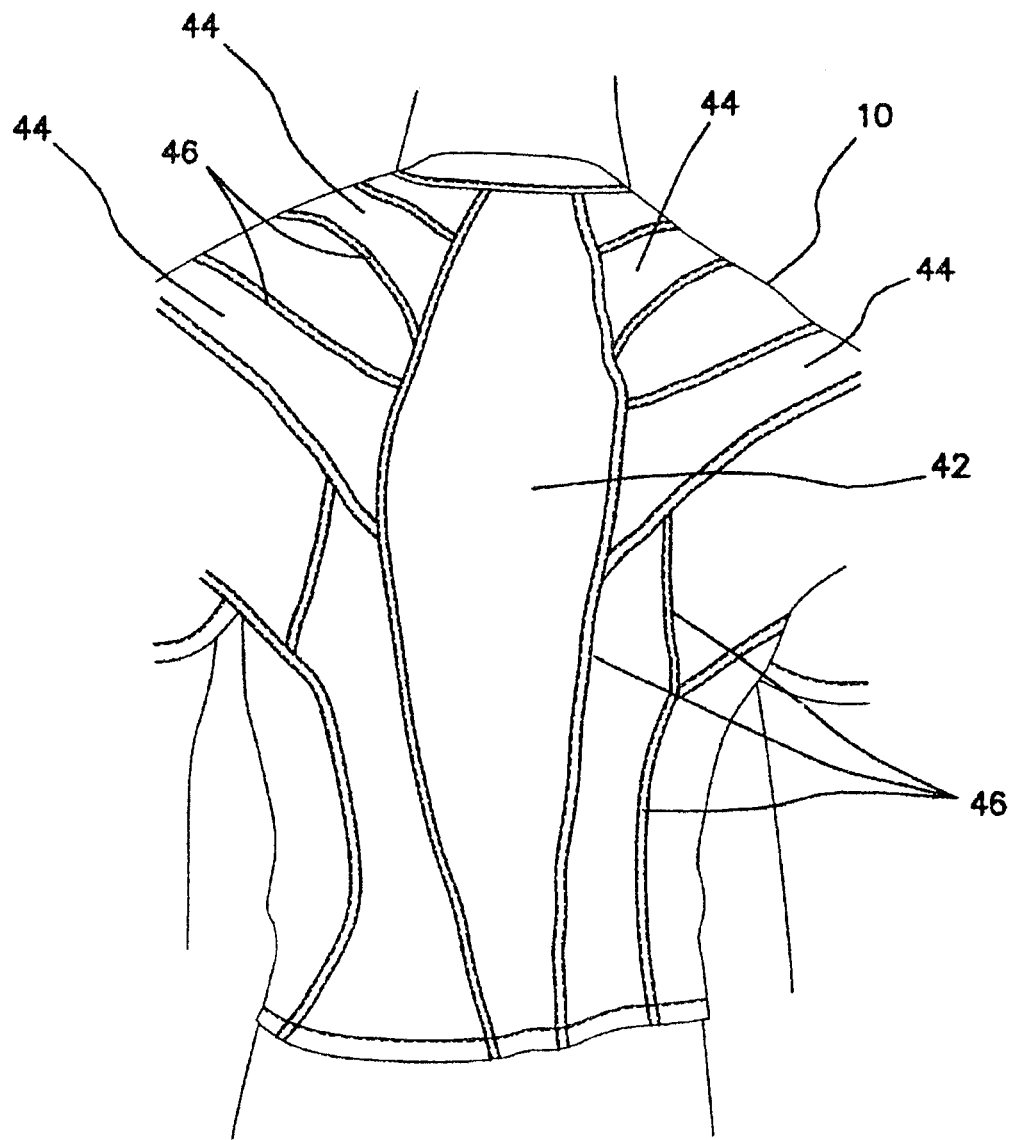
FIG. 8 is a posterior view of the embodiment of FIG. 7.

Still another, presently preferred, embodiment of the garment 10 of the invention is illustrated in FIGS. 7 and 8. This embodiment is similar in many respects to the prior embodiments, but employs an elastic or stretch band or panel 42 which extends along substantially the entire length of the spine of the wearer, as shown in FIG. 8. Straps 44 are also provided, which extend, as shown, from the panel 42 up and over each shoulder of the user. The straps 44 preferably extend over the shoulder and onto the anterior side of the garment, as shown in FIG. 7. The panels 42, 44 are integrated into the remainder of the garment 10 by stitching 46. This configuration has been found to substantially increase and enhance the cues which proprioceptively stimulate the user's brain and body to a corrected posture.

Significantly, in all of the illustrated embodiments, the posterior panel of the shirt is smaller than the anterior panel (which are sewn together), preferably by about two inches. This increases the retractive pull of the shirt, and thus the compression applied to the user's skin.

Viscoelastic pads for stimulating the user's proprioception may optionally be employed in each of the illustrated embodiments, on the inside surface thereof, either permanently or releasably mounted thereto, for contacting the user's skin at strategic locations in order to increase the proprioceptive effect of the garment. These pads, preferably made of silicone, have a skin-contacting surface which is grooved or otherwise modified to improve tactile response, using an acupuncture-type approach. The pressure generated by the garment 10 creates an acupressure effect. In one embodiment, two of these pads may be deployed on the chest region of the user, while two others are deployed on the scapula border, but, of course, the strategic locations and numbers of pads may be varied in accordance with specific therapeutic objectives.

To summarize, the present invention uniquely functions, due to its proprioceptive approach, to address the following conditions:
a) upper trapezium pain,
b) rotator cuff weakness, by optimizing scapular position to improve the rotator cuff muscle,
c) mid-thoracic pain, by decreasing tension in the periscapular muscles,
d) scapular dyskinesis,
e) biceps tendinitis,
f) thoracic outlet syndrome,
g) impingement syndrome, and
h) glenohumeral instability.

Figure 9:
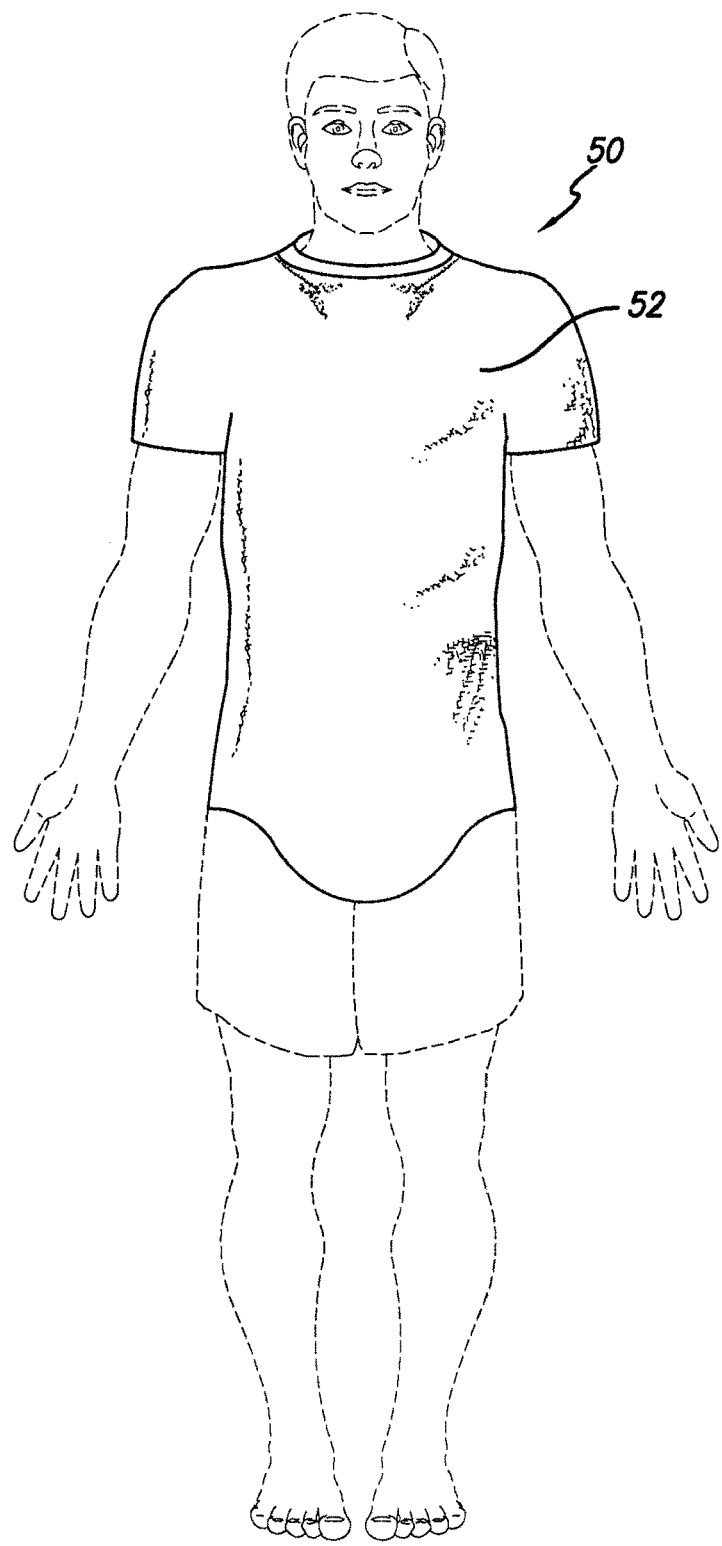
FIG. 9 is a front elevational view of a garment in accordance with another embodiment of the present invention.
Figure 10:
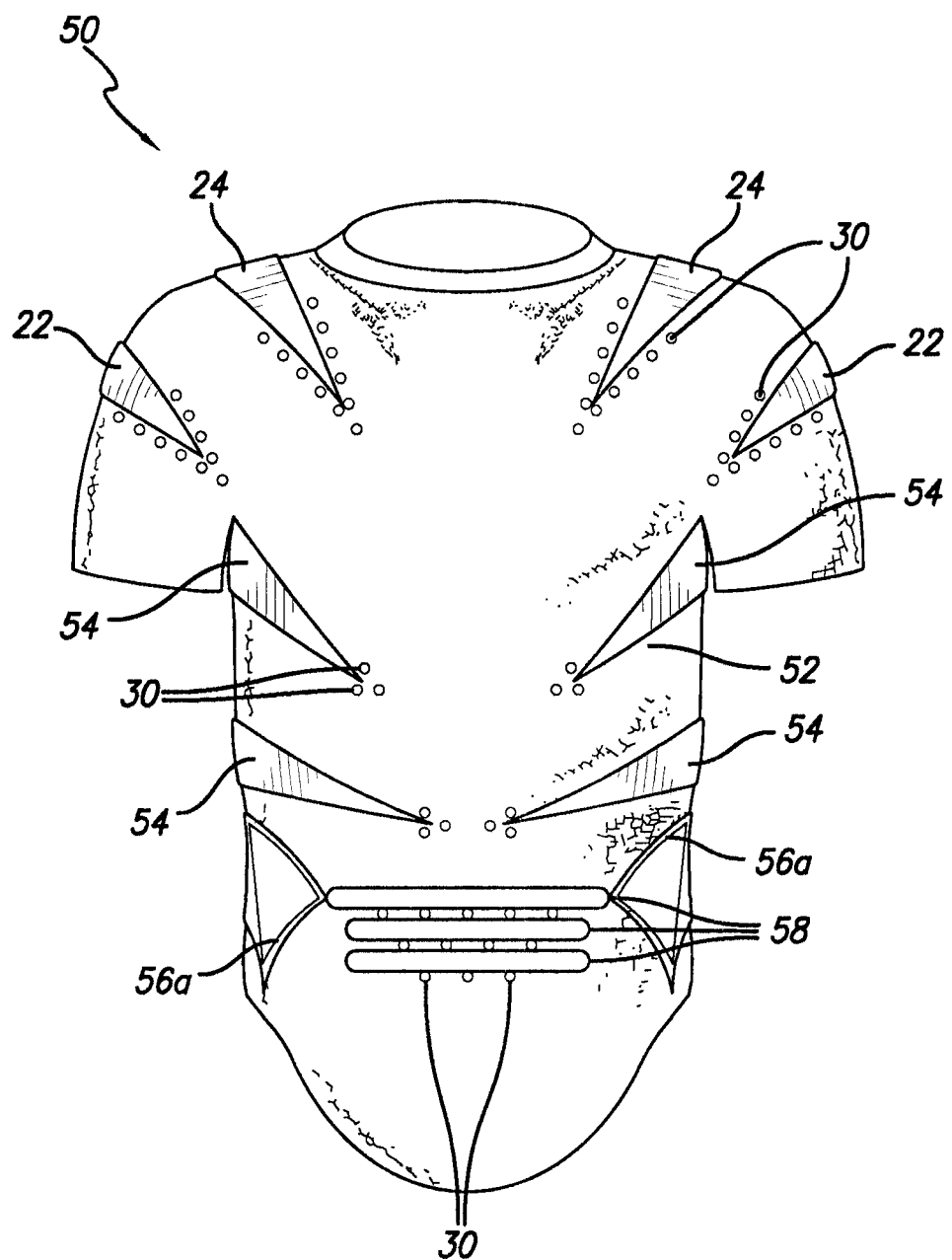
FIG. 10 is a front elevational view of the garment of FIG. 9 shown inside out to show the features on the inside of the garment.
Figure 11:
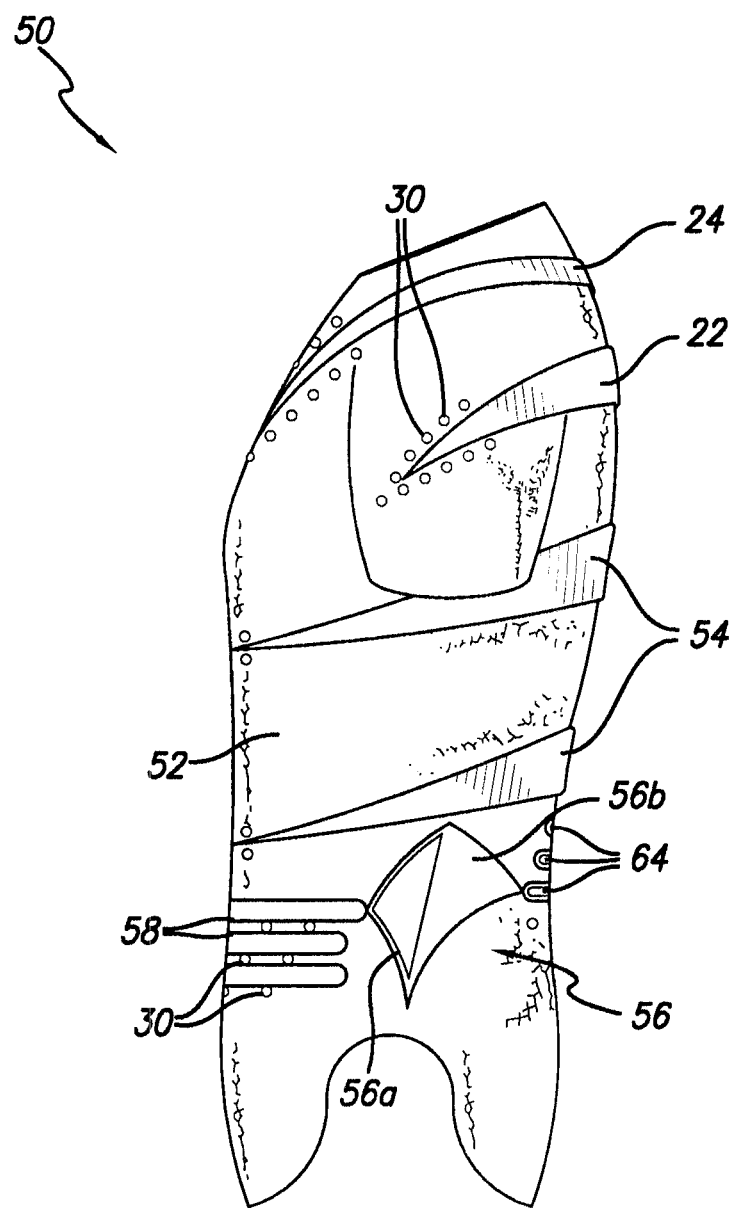
FIG. 11 is a left side elevational view of the garment of FIG. 9 shown inside out to show the features on the inside of the garment.
Figure 12:
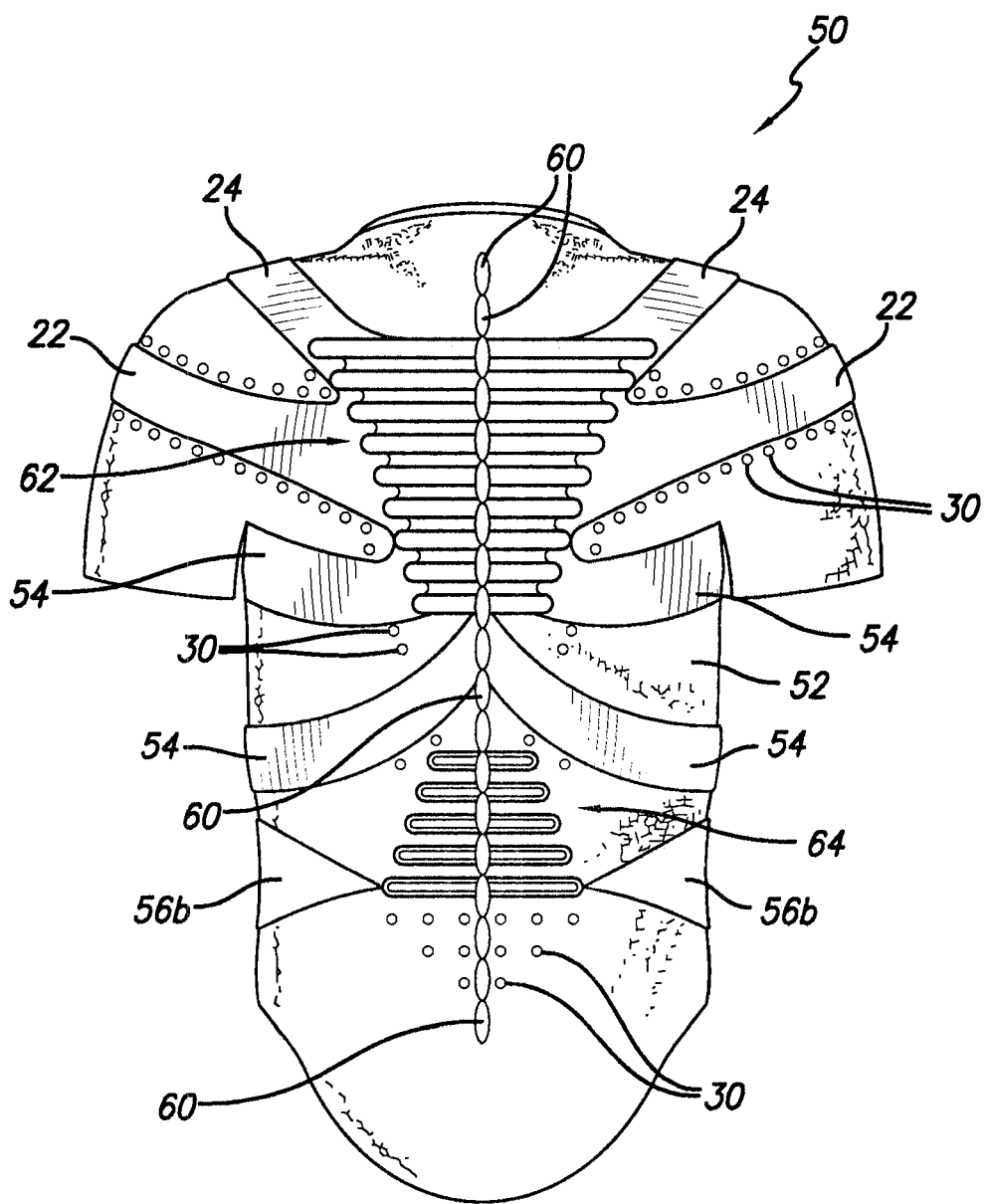
FIG. 12 is a rear elevational view of the garment of FIG. 9 shown inside out to show the features on the inside of the garment.

FIGS. 9-14 show another embodiment of a posture correcting or sensory motor system stimulating garment or shirt 50. As shown in FIG. 9, in a preferred embodiment, the garment 50 looks like a normal shirt from the outside, but includes features for stimulating the sensory motor system on the inside, as shown in FIGS. 10-12. However, this is not a limitation on the present invention. In a preferred embodiment, the main body portion, base portion or outer layer 52 of the garment 50 is formed as a shirt and is fabricated from a material such as polypropylene, LYCRA®, spandex, nylon or the like. Any material that allows the garment 50 to be form fitting is within the scope of the present invention. And, as described below, the proprioceptive or sensory motor stimulating features are affixed to the inside surface of the main body portion 52. In a preferred embodiment all of the proprioceptive or sensory motor stimulating members (including, but not limited to straps 22, 24 and 54, bands 18, 42, 58, 62 and 64, patches 14, 38 and 60, plates 56, neuro nubs 30, darts 26, viscoelastic tape 28—sometimes referred to collectively herein as "sensory motor stimulation members") are comprised of a material that alters and controls the amount of stretch in the base fabric (comprising the main body portion 52) of the garment 50 and prevents the normal stretch of the skin (in contact with a sensory motor stimulation member) when the wearer moves, thereby stimulating the wearer's cutaneous nerve receptors to cause the wearer's muscles to respond appropriately. For example, any elastomeric material, a thermo-elastic plastic, rubber or a material such as FABRIFOAM® can be used. The normal stretch of the skin is the amount of movement the skin makes when a person without a garment on moves. In another embodiment of the present invention, the shirt can comprise an entire layer of the sensory motor stimulating material (grip material) as the outside layer and a plurality of "non-grip patches" on the inside thereof. This is essentially the opposite of the embodiment described herein. The "non-grip" portions are the portions of the garment where no sensory motor stimulation is desired.

Figure 13:
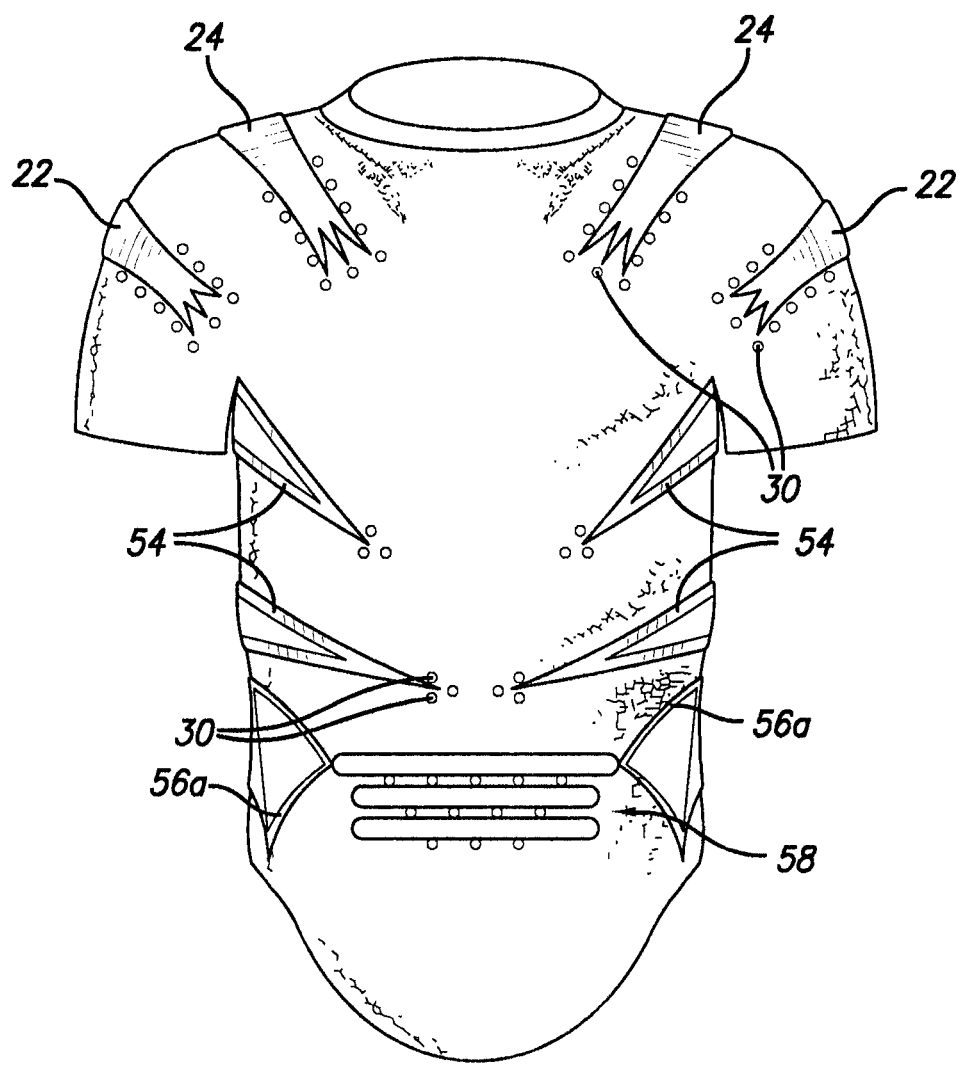
FIG. 13 is a front elevational view of a variation of the garment of FIG. 9 shown inside out to show the features on the inside of the garment.

As shown in FIG. 10, the garment 50 preferably includes at least one upper arm strap 22, at least one shoulder strap 24 and at least one serratus strap 54. These straps 22, 24 and 54 are similar to those described above. In a preferred embodiment, the straps 22, 24 and 54 end in a point that is positioned over a muscle attachment point. For example, the shoulder strap 24 end point is located over the pectoralis minor and the upper arm strap 22 is located over the infra spinitas teres minor In a preferred embodiment, the ends of the serratus straps 54 are located over the end of the rib cage. The upper serratus strap 54 is positioned over the serratus attachment and the lower strap 54 is positioned over the inter costal. As shown in FIG. 13, in another embodiment of the invention, the straps 22 and 24 (or any of the other straps described herein) can also end in multiple points or tentacles.

The straps 22, 24 and 54 are placed on the inside surface of main body portion 52 so the straps 22, 24 and 54 make direct contact with the nerve receptors in the skin. As described above, the shoulder straps 24 contact the skin over and below the corocoid process of the scapula (muscle attachment of pectoralis minor and short head of biceps and are saturated with acupuncture points) and traction the skin, superior and posteriorly causing the muscles that are attached to the corocoid process to lengthen and open while simultaneously causing a natural reflex called reciprocal inhibition to occur instantly. In use, this causes the opposing muscles to posteriorly tilt the scapula back into its natural position, which increases the joint space. Also, the muscles that extend the neck, upper and mid-spine, contract, tone and optimize the natural linear S-curve of the spine which decreases the common "head carried forward, slumping, failed posture" that often causes pain and disease in humans.

As shown in FIG. 10, the upper arm straps 22 are preferably adjacent the rotator cuff and stimulate external rotation of the humerus within the glenoid cavity. They also stimulate contraction of the horizontal scapular stabilizing muscles. Most shoulders are prone to internal rotation and lack tone in the muscles that resist rolling the shoulders internally. By placing the upper arm straps 24 on the weakened muscle, the strap 24 causes the muscle to contract and tone and support. In use, this helps align the humerus within the glenoid and improves muscle strength, range of motion, proprioception and therefore, function of the shoulder joints.

As shown in FIGS. 10-14, the shirt 50 also includes diamond shaped plate 56. In a preferred embodiment, plate 56 has a front portion 56a that is outlined and a rear portion 56b that is solid. Outlined means that a portion of the plate is cut out, thereby creating a narrow band of material that borders or outlines the diamond shape. As can be seen in FIG. 11, a triangle is defined in the front portion 56a of the plate 56 by the narrow band of material. This is not a limitation on the present invention. In another embodiment, the entire plate 56 can be solid or the entire plate 56 can be outlined. It will be understood that any of the proprioceptive or sensory motor stimulation members (including, but not limited to straps 22, 24 and 54, bands 58, 62 and 64, patches 60, plates 56, neuro nubs 30) can be either solid or outlined. See, for example, FIG. 13, which shows the serratus straps 54 in outlined form. It will be understood that outlined sensory motor stimulation members provide for more motion and encourage movement and solid sensory motor stimulation members encourage stability and compression and activate muscle tone.

It will be understood that each plate 56 (on the left and the right sides of the shirt) extend over the transverse abdominus and the internal oblique muscles, both of which play a key role in core stability.

The shirt 50 also preferably includes at least one and preferably a plurality of lower abdominal bands 58. As shown in FIG. 10, the abdominal bands 58 are solid. However, in another embodiment, they can be outlined. The bands 58 are positioned over the lower abs or the lower rectus abdominus and just below umbilicus. In use, the bands 58 cue the lower abs to contract, which results in a reflex action that relaxes the normally hypertoned hip flexors (part of the lower crossed syndrome) and the muscles of the lower back. This helps place the lumbosacral spine in optimal alignment and engages the core (hips, pelvis, and lumbosacral spine) to function optimally.

Figure 14:
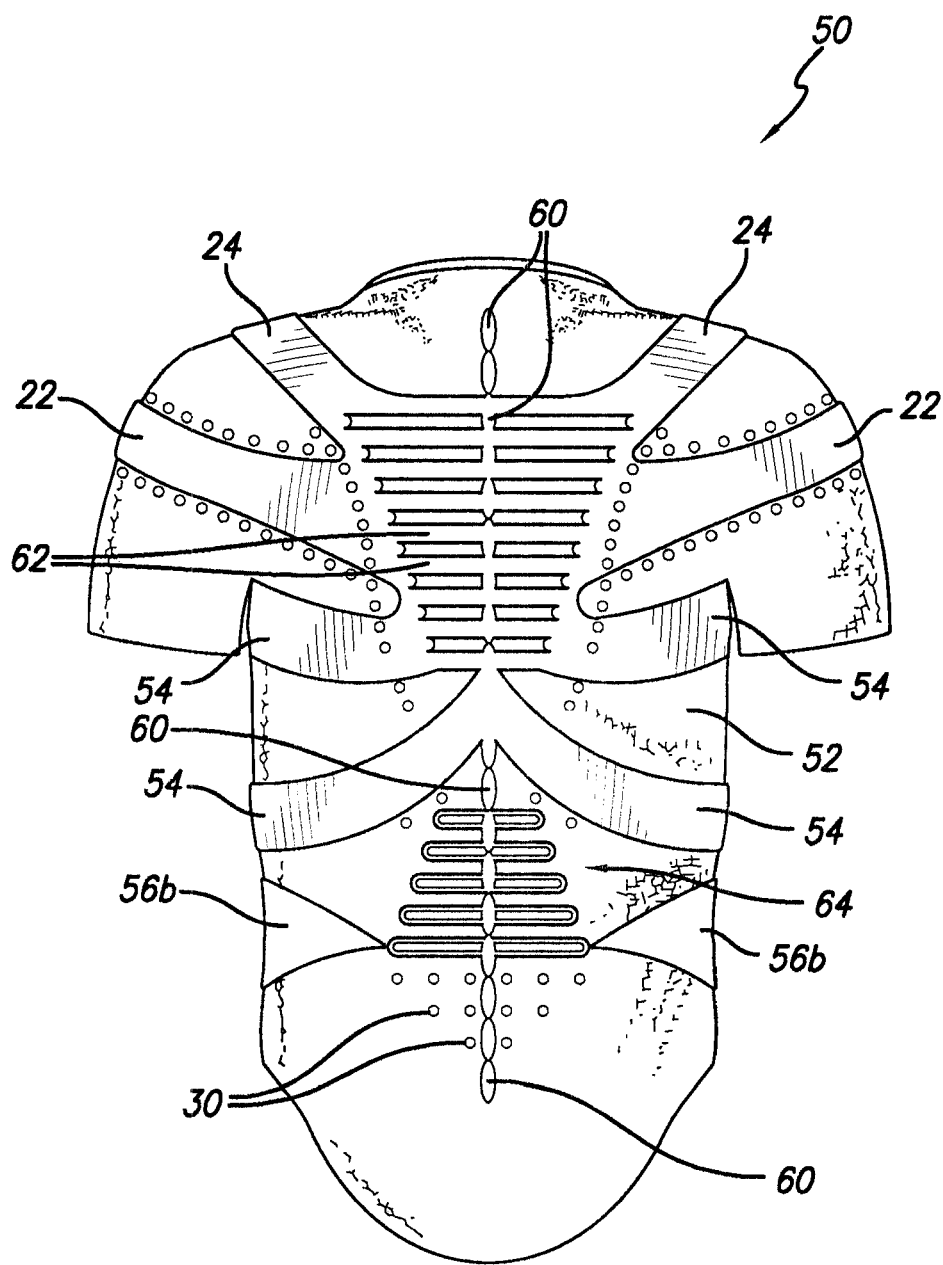
FIG. 14 is a rear elevational view of a variation of the garment of FIG. 9 shown inside out to show the features on the inside of the garment.

As shown in FIG. 12, in a preferred embodiment, the shirt 50 includes a plurality of vertebra patches 60. The patches 60 are preferably positioned over each individual vertebrae in the thoracic and lumbar spine and are interconnected to each other. In another embodiment, the patches may only be positioned over selected vertebrae in the thoracic and/or lumbar spine. In yet another embodiment patches can be positioned over the vertebrae in the cervical spine and/or the lumbar/lumbo sacral spine. As shown in FIG. 14, in another embodiment, the patches 60 can also be connected to the scapular bands 62 (described below). In use, the patches 60 assist in extension of the thoracic spine and integrate coupled movement by cueing tone to enhance the function of the extensor muscles to provide stability and normal movement patterns to the joints of the cervical and thoracic spine along with the right and left scapulothoracic joints. In other words, the patches in the garment that are positioned over the thoracic vertebra prevent the normal stretch of the skin when the head drops forward. This is what stimulates the cutaneous nerve receptors to cause the muscles to respond appropriately.

As is best shown in FIG. 12, the shirt 50 also includes at least one and preferably a plurality of scapular bands 62. The scapular bands 62 extend over the inter scapular muscles (middle trapezious, lower trapezious, rhomboids major and rhomboids minor) to provide constant cue to these muscles to assist in keeping scapulae in ideal natural movement planes during static and dynamic movement activities.

As is best shown in FIG. 12, the shirt 50 also includes at least one and preferably a plurality of lumbar spine bands 64 for proprioceptive awareness of muscle tone and alignment of the lumbar spine and specific compression of the lumbar spine structures. The lumbar spine bands 64, which are preferably outlined (but can be solid), together with the lower abdominal bands 58, which are preferably solid, links the abdominal section of core muscles together providing sensory motor feedback for alignment support and function.

The shirt 50 can also include neuro nubs 30, as described above. The neuro nubs 30 are preferably placed in specific areas with richly innervated tissues that correspond to specific acupuncture points to help stimulate circulation, energy and "chi" through areas prone to tension, over use and dysfunction. The nubs 30 also assist in decreasing migration of the garment as the wearer moves freely through all normal range of movements.

As can best be seen in FIGS. 11 and 12, many of the sensory motor stimulation members (e.g., straps 22, 24 and 54) extend in a spiral or helical manner about the axis of the shirt. This causes the skin, muscle and/or tissue under the straps 22, 24 and 54 to be moved or stimulated in a spiral direction when worn. As described above in the Summary section, this spiral movement is physiologically beneficial. The spiral or helix may extend at any angle. As discussed above, the Fibonacci numbers, hence the helix/spiral shape is important in nature (e.g., the human body) for the smooth flow of energy and enhances human physiology and function. As shown in FIGS. 10-14, in keeping with the spiral/helical concept, in a preferred embodiment, straps 22, 24 and 54 all generally extend toward or point toward the wearer's opposite hip. In other words, if all of the right straps 22, 24 and 54 were continued downwardly, they would meet at the left hip of the wearer. And, if all of the left straps 22, 24 and 54 were continued downwardly, they would meet at the right hip of the wearer. This is preferable for the portions of the straps 22, 24 and 54 on the back and front of the shirt. This is not a limitation on the invention. In other embodiments, the straps can extend at different angles. This orientation of the straps 22, 24 and 54 is in accordance with nature's rules of alignment and energy flow (i.e., the Fibonacci Numbering System discussed above). This helps achieve anatomical alignment with improved and more focal stimulation using the body's natural diagonal and spiral angles of alignment and movement. This angle of orientation along with other features, such as the lower abdominal toning cue (via lower abdominal bands 58); the anatomically specific thoraco-lumbo-sacral support (via vertebra patches 60 and lumbar bands 64) stimulates thoracic spinal extensor muscles and provides proprioceptive feedback to the T-L-S spine. The addition of the transverse abdominis and the internal oblique plate 56 stimulates these important core stabilizing muscles. "Outlined" horizontal bands 64 add specific, moderate compression throughout the lumbar spine and upper core by preferably connecting/linking to the transverse abdominis and internal oblique muscle plates 56 which preferably connects/links to the "solid" horizontal lower abdominal bands 58.

It will be understood that in manufacturing the garment 50, the various sensory motor stimulation members can be separate pieces of material or can be interconnected or a single piece. For example, FIG. 12 shows that the patches 60, scapular bands 62 and straps 22, 24 and 54 are all separate pieces of material. However, FIG. 14 shows that they are all a single piece of material.

Figure 15:
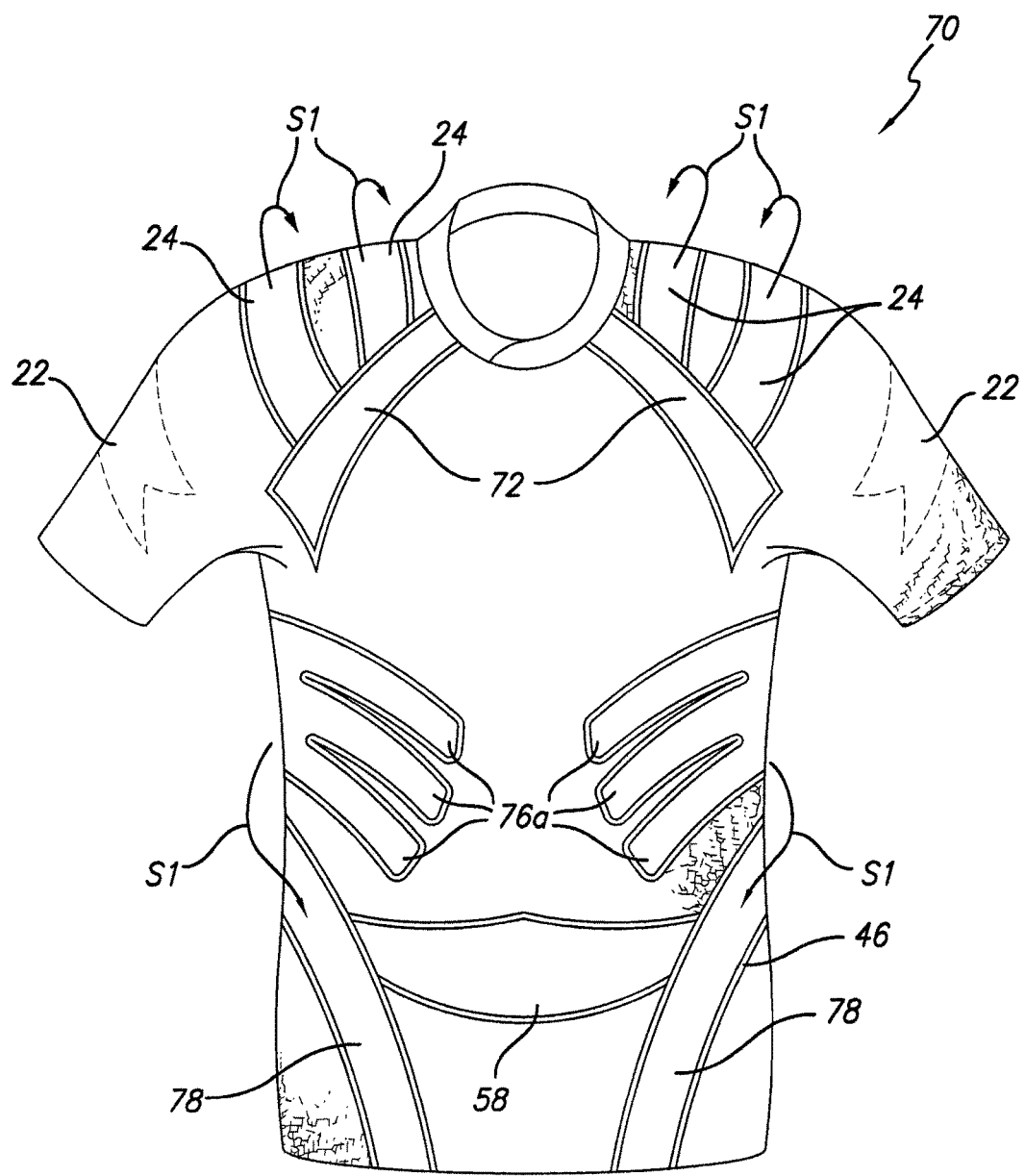
FIG. 15 is a front elevational view of a garment in accordance with another embodiment of the present invention.
Figure 16A:
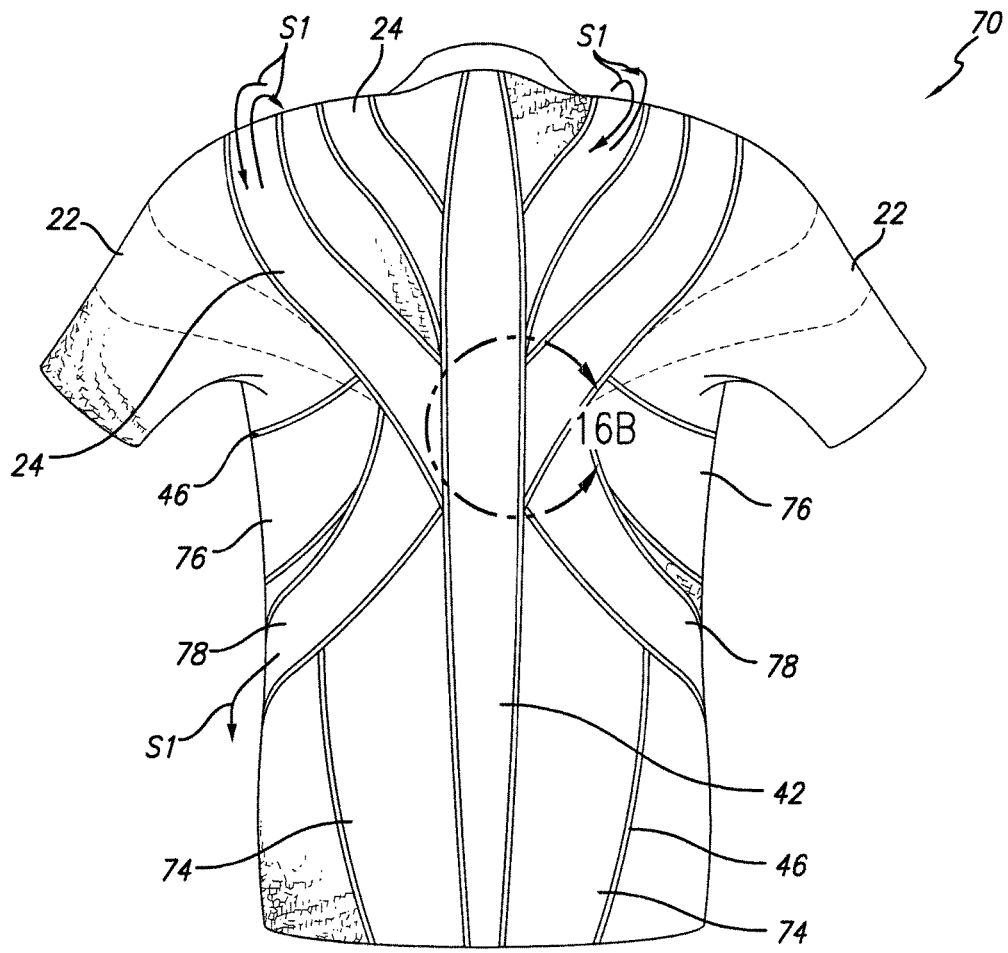
FIG. 16A is a rear elevational view of the garment of FIG. 15.
Figure 16B:
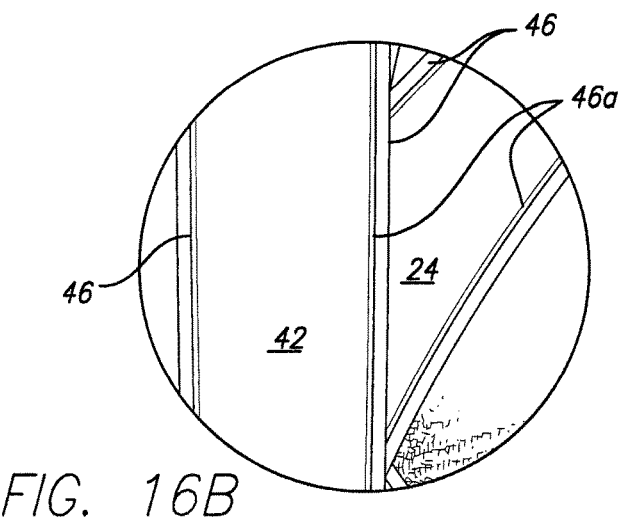
FIG. 16B is a detail view taken from FIG. 16A.
Figure 17:
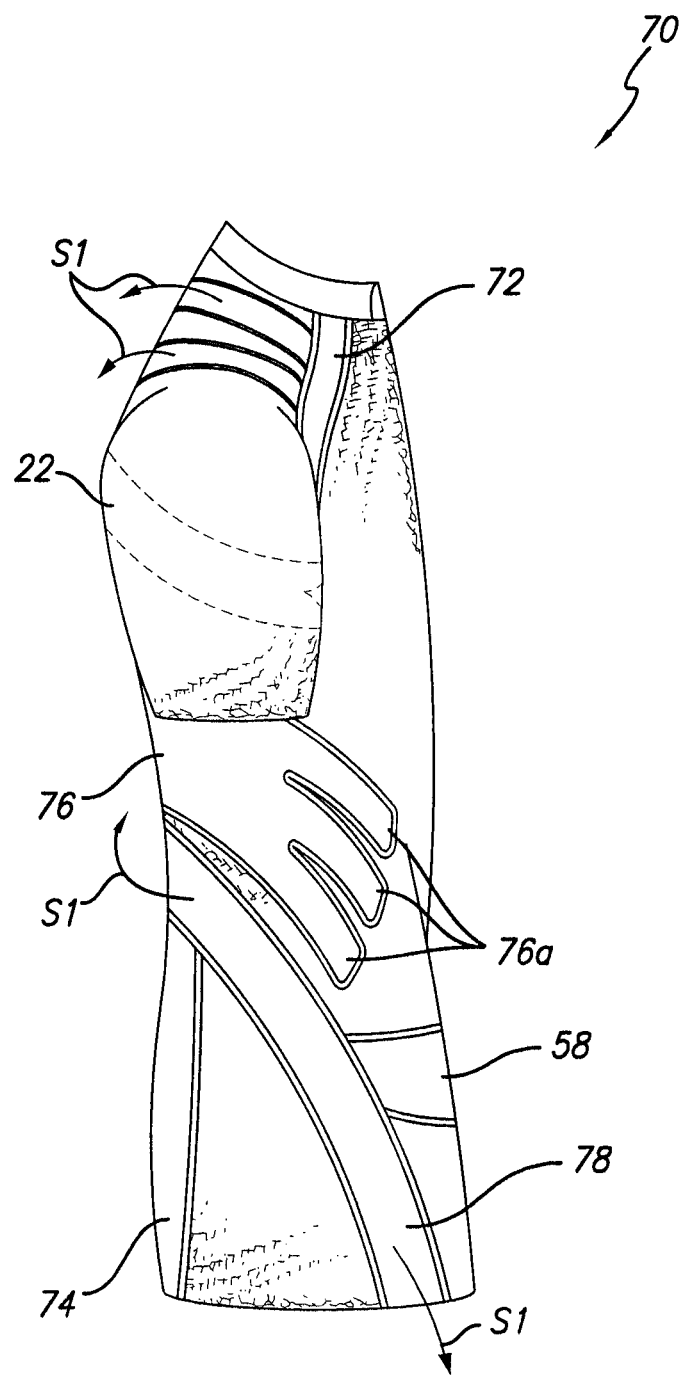
FIG. 17 is a right side elevational view of the garment of FIG. 15.

FIGS. 15-17 show another embodiment of a posture correcting or sensory motor system stimulating garment 70. In some embodiments, the garment 70 includes a form-fitting shirt that is made of an elastomeric material, and fits contours of the wearer's torso. The garment 70 combines features taught in the various embodiments described above and, in particular, includes bands that extend in a spiral or helical shape around the shirt (and around the axis of the main body portion of the shirt) and, therefore, the torso of the wearer (see the arrows labeled S1 in FIGS. 15-17). Therefore, the description set forth above with respect to the various portions and components of the garments/shirts, the placement of straps and/or bands and the muscles and other parts of the anatomy that they affect is all applicable here. It will be understood that this embodiment shows that the shirt can include both straps, bands, patches, etc. that are sewn into the shirt (similar to the embodiment shown in FIG. 8) or that are secured to the inside (similar to the embodiment shown in FIG. 10). For example, rotator cuff bands 22 are shown in hidden lines to show that they are secured to the inside of the shirt and are not sewn in, unlike the remainder of the bands. It will be understood that any combination of sewing and securing on the inside is within the scope of the present invention. Alternatively, in some embodiments, the rotator cuff bands 22 are secured to the outside of the shirt, and the remainder of the bands is secured to the inside of the shirt. In some embodiments, all bands are secured to the outside of the shirt. In some embodiments, all bands are secured to the inside of the shirt.

This embodiment is similar in many respects to the prior embodiments and employs an elastic or stretch band or spine band, strap or panel 42 which extends longitudinally across the posterior portion of the shirt from a neck region of the shirt toward a waist portion of the shirt (which, when worn by a wearer, corresponds to a waist of the wearer), as shown in FIG. 8. The spine band 42 is attached to the posterior portion of the shirt, and is fabricated from an elastomeric material. This spine band 42 provides the base the other bands (e.g., 24, 22, 76, 78, etc.) pull from (see the arrows labeled S1 in FIGS. 15-17). When the garment 70 is in use (e.g., worn by a wearer), the spine band 42 stimulates cutaneous nerve receptors (e.g., mechanoreceptors and/or nociceptors) in a portion of a wearer's skin underneath the spine band 42. The garment 70 is configured to allow a natural motion of the wearer, while providing a viscoelastic resistance in a longitudinal direction along the spine band 42 (e.g., the spine band 42 provides resistance when the wearer bends forward). In some embodiments, the garment provides viscoelastic resistance in multiple directions, but mainly in the longitudinal direction along the spine band 42. This configuration provides the effect of training body muscles for proper posture through muscle memory. When a wearer repeatedly maintains a good posture with the assistance of the garment for an extended period of time, it is believed that a long-term muscle memory is created, making it easier to maintain the good posture without conscious effort. The formation of the muscle memory may be explained by engrams, through which memory traces are stored in neural tissue in response to external stimuli. In contrast, poor movement patterns over time cause dysfunctional muscle memory patterns. A use of the garment 70, by improving one's movement patterns, can reverse this pathological trend.

In some embodiments, the garment 70 also includes at least one additional band. In some embodiments, the at least one additional band extends from the spine band 42. When the garment 70 is in use (e.g., worn by a wearer), the at least one additional band stimulates cutaneous nerve receptors in a portion of a wearer's skin underneath the at least one additional band. In some embodiments, the garment 70 is configured to allow a natural motion of the wearer, while providing a viscoelastic resistance in a longitudinal direction along the at least one additional band. In some embodiments, the garment provides viscoelastic resistance in multiple directions, but mainly in the longitudinal direction along the at least one additional band. This configuration provides the effect of training body muscles for proper posture through muscle memory.

In some embodiments, the spine band 42 is attached to the shirt, such that when in use (e.g., worn by a wearer), the spine band 42 applies a corrective force along the longitudinal direction of the band when the wearer is in a neutral posture. Such effect can be achieved by, for example, attaching (e.g., by stitching) the spine band 42 onto the shirt when the spine band 42 is elongated. Alternatively, portions of the spine band 42 can be attached (e.g., by stitching) to respective portions of the shirt such that the spine band 42 is stretched when the shirt is worn by the wearer. In some embodiments, the at least one additional band 42 is attached to the shirt, such that when in use (e.g., worn by a wearer), the at least one additional band 42 applies a corrective force along a longitudinal direction of the at least one additional band when the wearer is in a neutral posture. These configurations provide the effect of training body muscles for proper posture through muscle memory. Over time, these configurations promote coordination between the muscles and nervous system and improve human posture both statically and dynamically through repetition of quality movements that creates muscle memory.

In some embodiments, the at least one additional band includes shoulder bands 24, which extend, as shown, from the spine band 42 up and over each shoulder region of the shirt (which, when worn by a wearer, corresponds to each shoulder of the wearer) toward the anterior portion of the shirt. In some embodiments, shoulder bands 24 include inner shoulder bands and outer shoulder bands. In some embodiments, the at least one additional band includes rotator cuff bands 22, which extend, as shown, from the spine band 42 across respective upper arm regions of the shirt (which, when worn by the wearer, correspond to upper arms of the wearer). The bands 22 and 24 can extend over the shoulder and upper arm regions and onto the anterior side of the garment 70, as shown in FIG. 12. In some embodiments, when in use, the shoulder bands 24 provides a coupled direction of pull that influences the wearer's shoulders to move down and back allowing the scapulae to move towards their optimal, functional, and anatomical positions. In some embodiments, the bands 42, 22 and 24 are integrated into the remainder of the garment 70 by stitching 46. In an exemplary embodiment, the seams 46 are attached with flatlock stitching. The elastic can also be included at the hems, e.g., at the sleeves and waist. In a preferred embodiment, the stitching 46 can include elastic material therein 46a (as shown in FIG. 16B). The elastic material reduces migration of the garment 70 and adds to the proprioceptive effect. In some embodiments, specific placement and angle of bands are based upon anatomical origin and insertion of muscles and tendons and well known acupuncture meridians, which have high concentrations of neurological receptors and/or structures.

In some embodiments, the shirt is fabricated from a first elastomeric material, and the spine band 42 is fabricated from a second elastomeric material different from the first elastomeric material. In some embodiments, the shirt is fabricated from a first elastomeric material, and the spine band 42 and the at least one additional band are fabricated from a second elastomeric material different from the first elastomeric material. In some embodiments, the shirt is fabricated from a first elastomeric material, the spine band 42 is fabricated from a second elastomeric material different from the first elastomeric material, and the at least one additional band is fabricated from a third elastomeric material different from the first and second elastomeric material. In some embodiments, the shirt, the spine band 42, and the at least one additional band are fabricated from the same elastomeric material.

In some embodiments, the at least one additional band includes pectoral anchor bands 72, which are provided to hold and stabilize the front (anterior portion) of the garment 70 and to allow shoulder bands 24 to have an anchor so that the shoulder bands 24 pull in a spiral motion towards the posterior portion of the shirt, when the shirt is worn by a wearer (see the arrows labeled S1 in FIGS. 15-17). Pectoral anchor bands 72 typically extend from the neck region on the anterior portion of the shirt toward a chest portion of the shirt (which, when worn by a wearer corresponds to a chest of the wearer). Pectoral anchor bands 72 affect the major and minor pectorals and therefore are referred to herein as pectoral anchor bands 72. The pectoral anchor bands 72 can be made from FABRIFOAM®, polypropylene or the like. In some embodiments, rotator cuff bands 22 can be connected to the pectoral anchor bands 72. In some embodiments, each shoulder band 24 is connected at one end to the spine band 42 and at the opposite end to a respective pectoral anchor band 72.

In some embodiments, as shown in FIG. 15, the at least one additional band includes at least one abdominal band 58, positioned on the anterior portion toward the waist portion of the shirt, as described above.

In some embodiments, the at least one additional band includes quadratus lumborum panels 74 positioned on the posterior portion of the shirt toward the waist portion of the shirt. The quadratus lumborum panels 74 are designed to stimulate passive and dynamic support of paravertebral muscles that support and provide mobility, stability, endurance and strength in the thoracolumbar, lumbar and lumbosacral spine, respectively. In an exemplary embodiment, panels 74 can be made of FABRIFOAM®. In some embodiments, the quadratus lumborum panels are configured to support linear spinal alignment and are designed to stimulate and increase tones and fitness of the paravertebral thoracic extensor muscles.

In some embodiments, the at least one additional band includes serratus bands 76. Serratus bands 76 are similar to the serratus straps described above. In this embodiment, the bands 76 include a plurality of fingers or finger bands 76a that preferably point toward the opposite sides of the waist portion of the shirt or toward the waist portion of the shirt. Fingers 76a extend out over the abdominal muscles and also affect the transverse and oblique abdominals.

In some embodiments, the at least one additional band includes oblique bands 78. Oblique bands 78 are positioned similarly to plates 56 discussed above. For example, each oblique band 78 can be positioned such that it extends around a respective side of the shirt from the posterior portion of the shirt toward the waist portion and the anterior portion of the shirt in a helical pattern. Oblique bands 78 affect the transverse abdominals and the internal oblique muscles, both of which play a key role in core stability. As can be seen from a review of FIGS. 15-17, in a preferred embodiment, oblique bands 78 together with shoulder bands 24 form a spiral from the wearer's right shoulder down to the left hip and from the left shoulder to the right hip. The spiral or helical path of the oblique band 78 and corresponding shoulder band extend around the vertical axis of the shirt. In other words, in some embodiments, the garment includes two sets of bands, where each set includes a shoulder band and an oblique band, and each set is positioned in a helical pattern about a longitudinal axis formed through a center of the shirt.

In some embodiments, the at least one additional band (in particular, the at least one additional band connected to the spine band 42) applies shear force toward a middle section of the spine band, on the wearer's skin underneath the at least one band. It is noted that the spine band 42 has three sections: a top section, the middle section, and a bottom section. The three sections of the spine band 42 need not have equal lengths. The middle section of the spine band 42 does not need to be located exactly at the center of the spine band 42. In some embodiments, the at least one additional band pulls the wearer's skin toward the spine and stimulates paraspinal, interscapular, and core muscle activation, function, balance and alignment.

As discussed above, viscoelastic pads for stimulating the user's proprioception may optionally be employed in each of the illustrated embodiments, on the inside surface thereof, either permanently or releasably mounted thereto, for contacting the user's skin at strategic locations in order to increase the proprioceptive effect (or sensory motor stimulation effect) of the garment 70.

Essentially, the garment of the invention functions to create an exoskeleton for the user's body, thereby allowing for the sensory motor stimulation for proprioceptive awareness and treatment of strategic regions. Increased pressure is applied to these strategic body regions to perform the advantageous proprioceptive treatment. Prior art approaches involved mechanical treatment, i.e. physically manipulating portions of the body to desired configurations. This modern inventive approach instead induces a nervous system response through the application of strategic proprioceptive compression. There is no attempt to physically move large portions of the body. Instead, the garment does not move the wearer. It stimulates the sensory motor system to cause the muscles to do it naturally.

Figure 18:
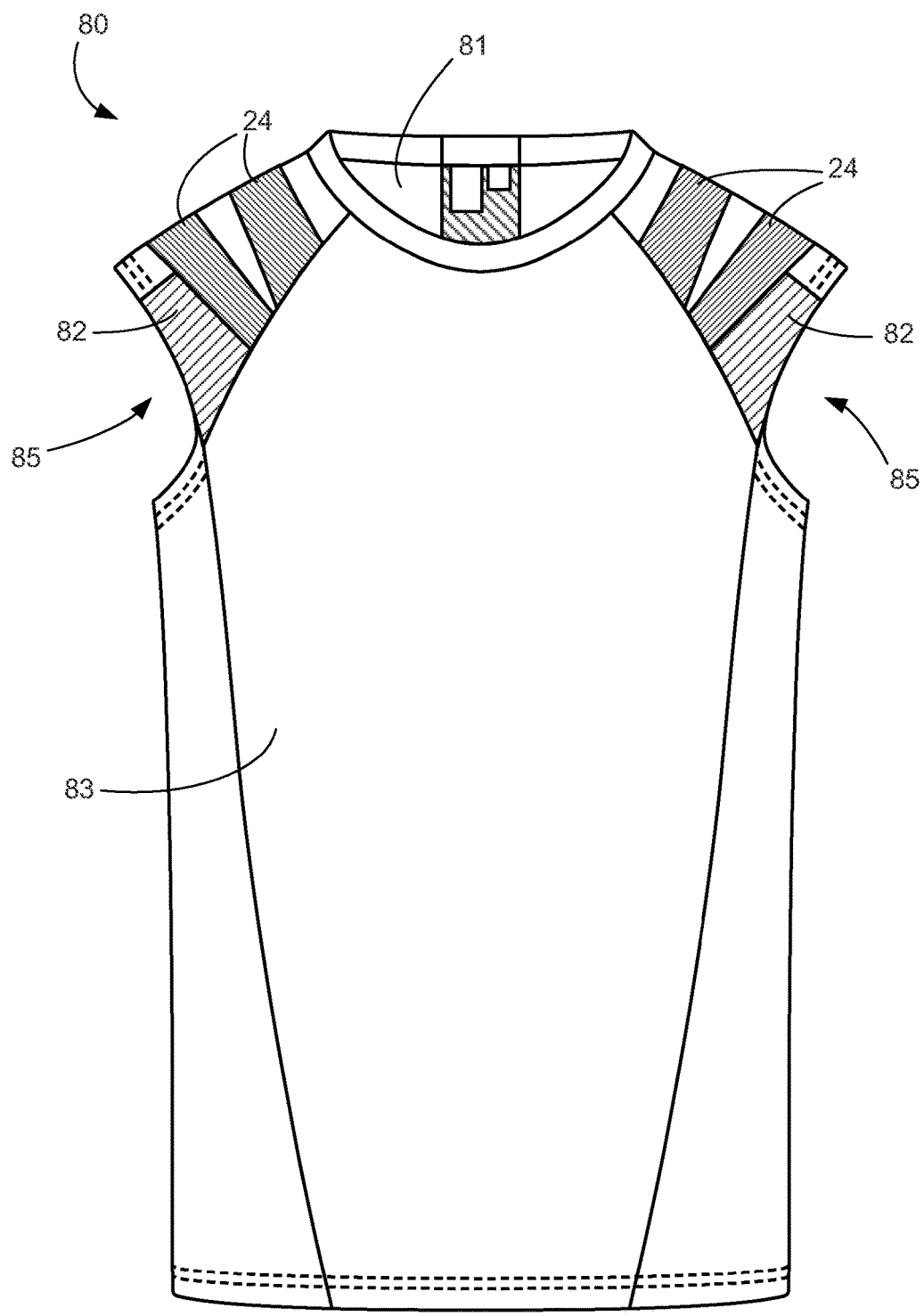
FIG. 18 is a frontal elevational view of a garment in accordance with some embodiments.
Figure 19:
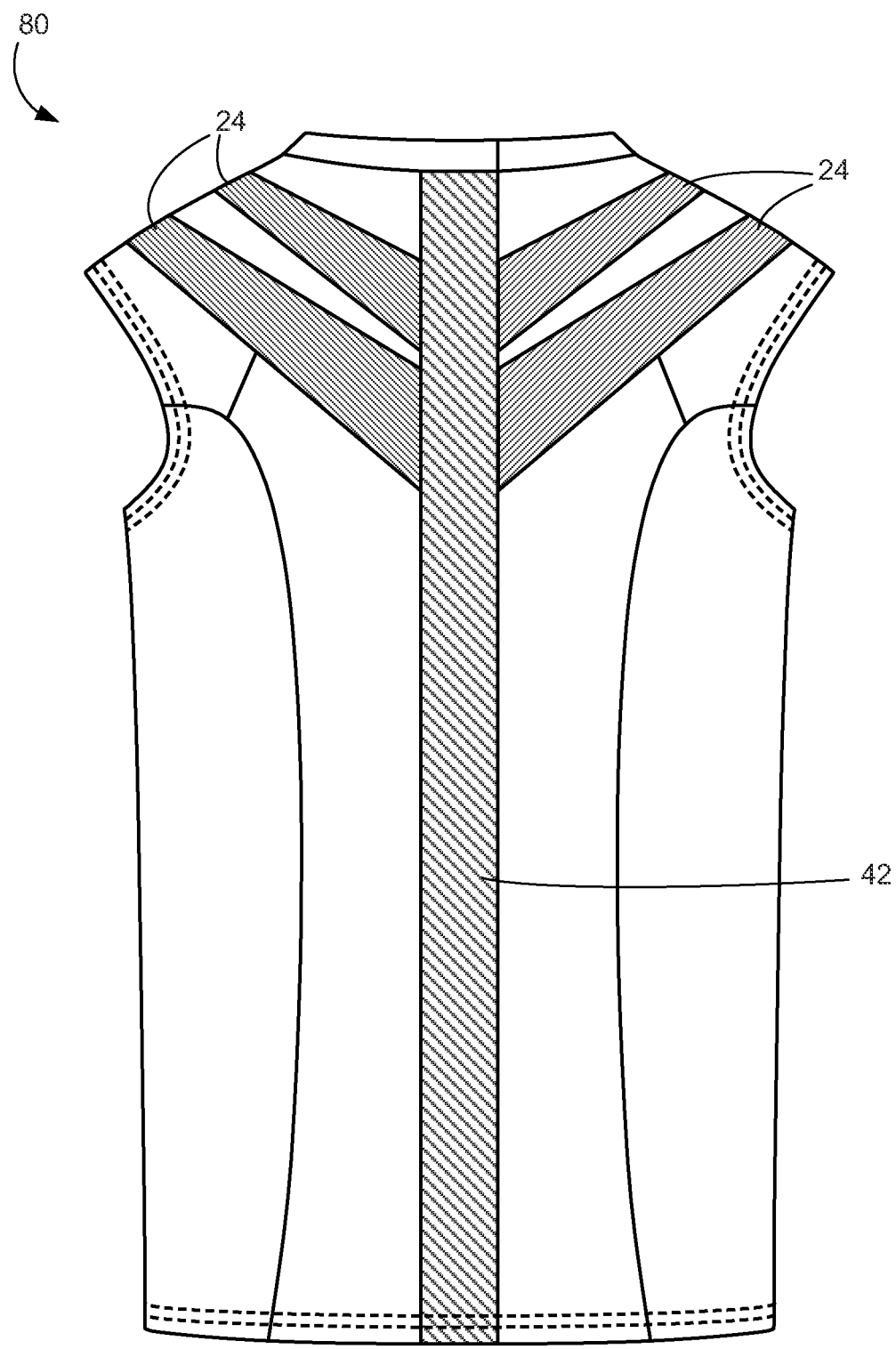
FIG. 19 is a rear elevational view of the garment of FIG. 18.
Figure 20:
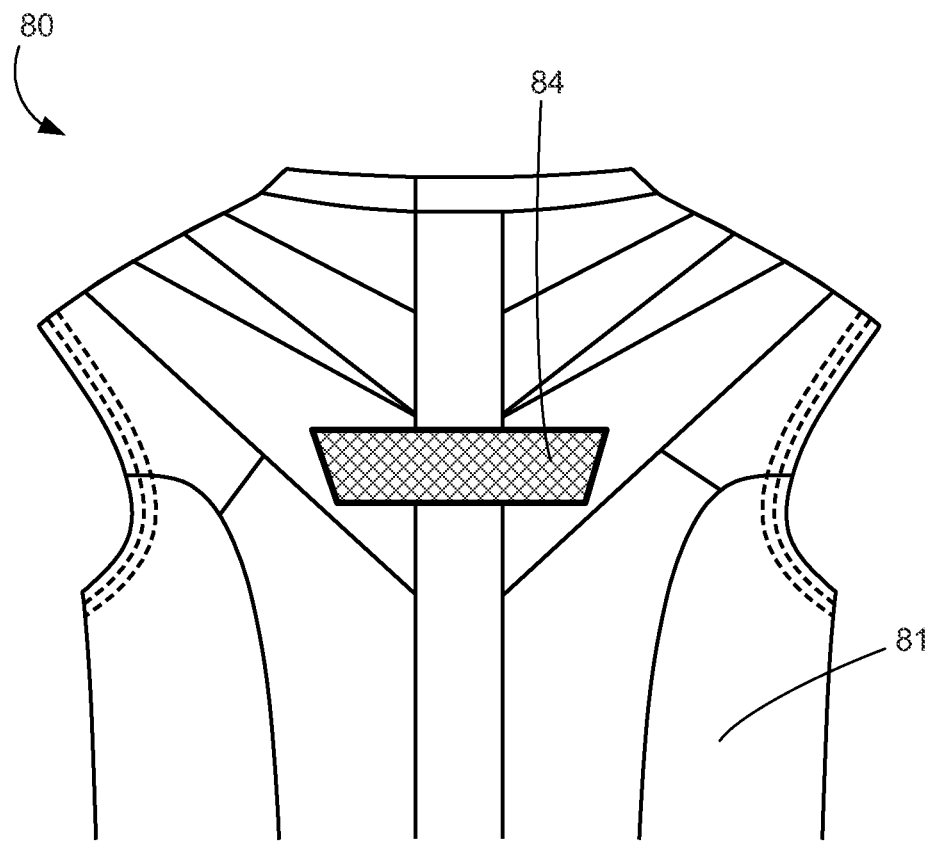
FIG. 20 is an inside view of the garment of FIG. 18.
Figure 23:
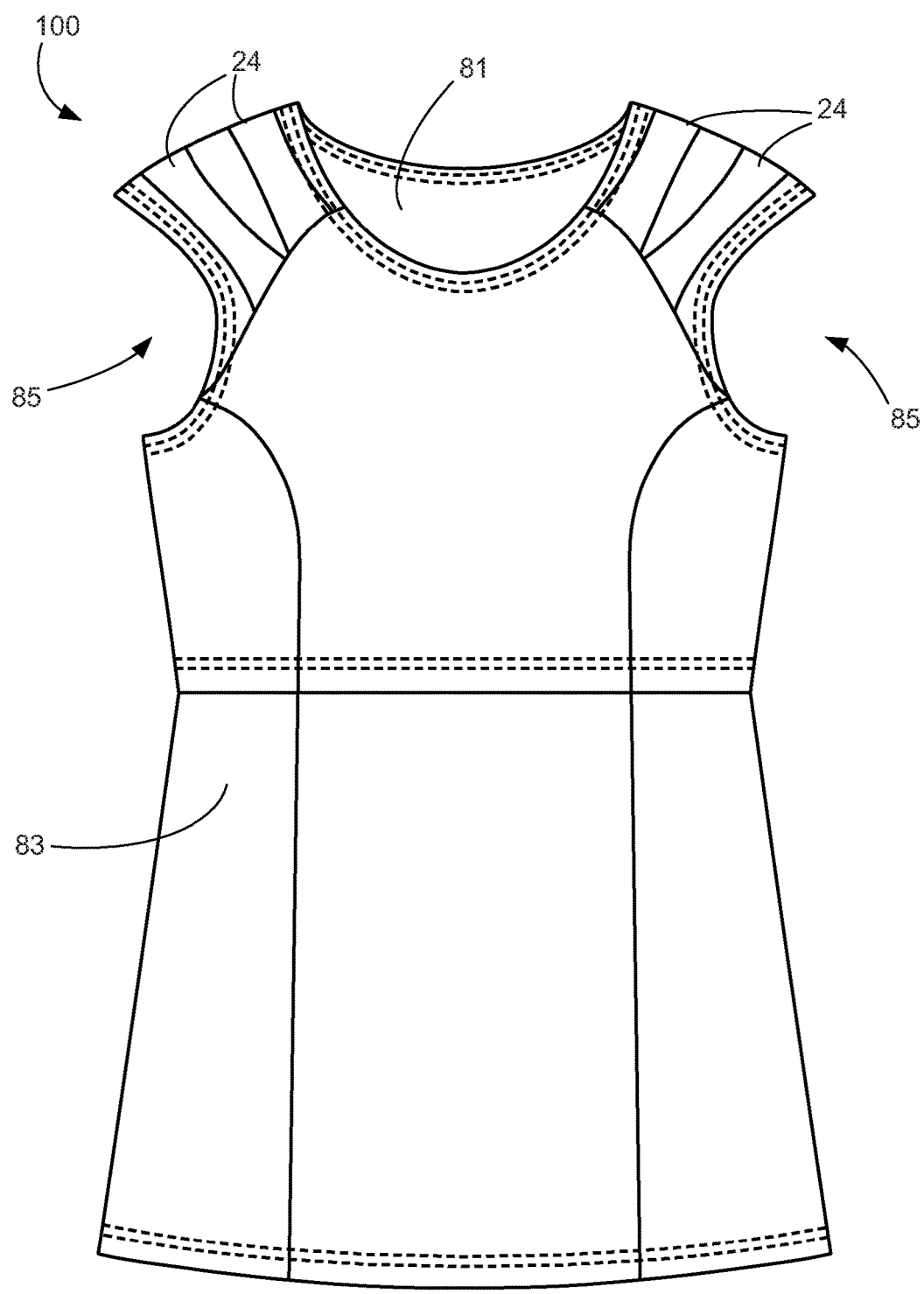
FIG. 23 is a front elevational view of a tank in accordance with some embodiments.
Figure 24:
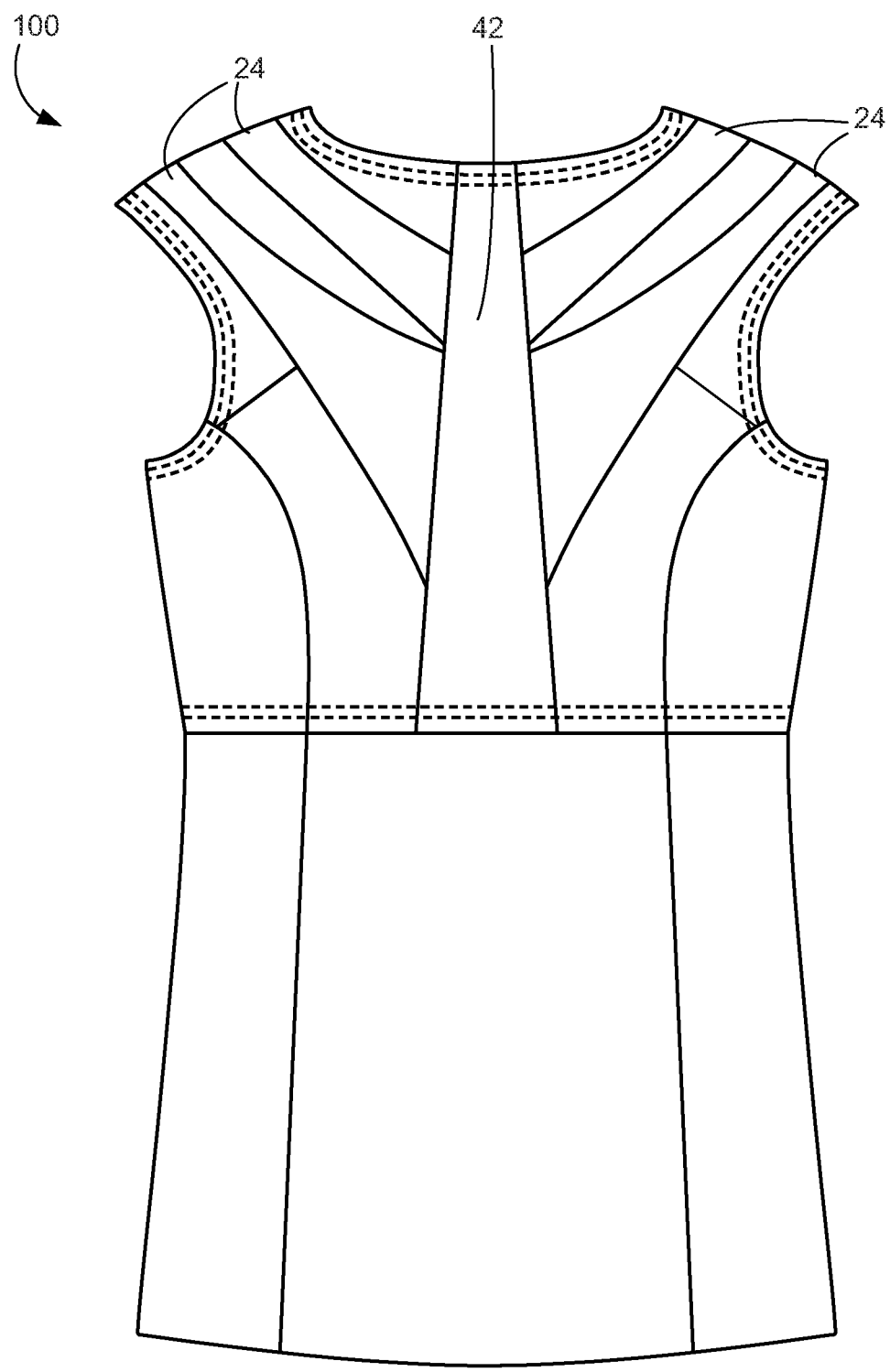
FIG. 24 is a rear elevational view of the garment of FIG. 23.

FIGS. 18-20 show a garment 80 in accordance with some embodiments. FIGS. 21A-21C and 22 show a garment 90 in accordance with some embodiments. FIGS. 23-24 show a garment 100 in accordance with some embodiments. In some embodiments, the garment 80, garment 90, and garment 100 share same or similar feature(s). Like reference numerals designate the same or similar parts or features throughout these figures. Description of such features are not repeated for brevity. In addition, many of the details of the embodiments described with respect to FIGS. 1-17 apply to the garment 80, garment 90, and garment 100, and therefore these details are not repeated for brevity. Similarly, the garment 80 may have many of the details of garment 90 and/or garment 100; the garment 90 may have many of the details of garment 80 and/or garment 100; and the garment 100 may have many of the details of garment 80 and/or garment 90. These details are not repeated for brevity.

FIG. 18 is a frontal elevational view of the garment 80. The garment 80 includes a first garment portion (e.g., the shirt layer). In some embodiments, the first garment portion is made from an elastomeric material. The first garment portion defines an inner surface 81, an outer surface 83, and two armholes 85. The inner surface is configured to contact the wearer when the wearer wears the garment 80. In some embodiments, the first garment portion comprises an anterior portion shown in FIG. 18 and a posterior portion shown in FIG. 19.

As shown in FIG. 18, one or more pads 82 are attached to the first garment portion of the garment 80 adjacent to each armhole 85. In some embodiments, the one or more pads 82 are fabricated from an elastomeric material. In some embodiments, the one or more pads 82 are fabricated from FABRIFOAM®. Notably, it has been found that the one or more pads 82 have the effect of reducing pain of the wearer.

In some embodiments, the one or more pads 82 are attached to the anterior portion of the first garment portion. In some embodiments, the one or more pads 82 are not directly attached to the posterior portion of the first garment portion. For example, the one or more pads 82 may be sown onto the anterior portion of the first garment portion, but not onto the posterior portion of the first garment portion.

FIG. 19 is a rear elevational view of the garment 80 (mostly showing the posterior portion of the garment 80). In some embodiments, the garment 80 also includes a spine band 42 attached to the posterior portion of the first garment portion and also fabricated from an elastomeric material. In some embodiments, the elastomeric material for the spine band is different from the elastomeric material in the first garment portion. Alternatively, the elastomeric material used for the spine band and the elastomeric material in the first garment portion may be the same. The spine band 42 extends longitudinally across the posterior portion of the first garment portion from a neck region of the shirt toward a bottom portion of the first garment portion along the spine of the wearer, such that in use, the spine band 42 stimulates cutaneous nerve receptors in a portion of a wearer's skin underneath the spine band.

In some embodiments, the garment 80 further includes at least one additional band attached to the first garment portion and also fabricated from an elastomeric material, such that in use, the at least one additional band stimulates cutaneous nerve receptors in one or more portions of the wearer's skin underneath the at least one additional band. In some embodiments, the elastomeric material used for the at least one additional band is different from the elastomeric material in the first garment portion. Alternatively, the elastomeric material used for the at least one additional band and the elastomeric material in the first garment portion may be the same.

In some embodiments, the at least one additional band extends from the spine band 42 toward the wearer's shoulders, e.g., shoulder bands 24.

In some embodiments, the garment 80 includes at least two shoulder bands 24 having a shape of a strip, each radiating from the spine band and extending towards a respective shoulder region of the first garment portion toward the anterior portion of the shirt. The shoulder bands 24 are used to stimulate cutaneous nerve receptors in a portion of a wearer's skin underneath the shoulder bands 24.

In some embodiments, the shoulder bands 24 include inner shoulder bands and outer shoulder bands, where the inner shoulder bands are positioned between the outer shoulder bands (e.g., FIG. 19).

FIG. 20 is an inside view of the garment 80 (the garment 80 turned inside-out). Located on a portion of the inside surface of the garment 80 is an inner layer 84. Typically, the inner layer 84 is made from a material that stimulates the sensory receptors in the wearer's skin. In some embodiments, the inner layer 84 is made from plastisol. In some embodiments, the inner layer 84 is formed by spraying the plastisol on the inner surface 81 of the first garment portion. In some embodiments, the inner layer 84 is made from silicone. In some embodiments, the inner layer 84 is formed by silk screening the silicone on the inner surface 81 of the first garment portion.

In some embodiments, the inner layer 84 has a predefined shape, such as a trapezoidal shape. In some embodiments, the inner layer 84 has a predefined pattern within the predefined shape, such as a grid pattern, a mesh pattern, and/or a honeycomb pattern. In some embodiments, the inner layer 84 has a predefined surface roughness or properties such that the friction increases between the inner layer 84 and the wearer's skin. Thus, in some embodiments, the inner layer 84 keeps the garment in place (i.e., the inner layer 84 reduces the migration of the garment when in use).

In some embodiments, the inner layer 84 is configured to contact a scapular region of the wearer. The scapular region has many nerve endings, and thus, placing the inner layer 84 in contact with the scapular region of the wearer's back improves the stimulation of sensory receptors.

In FIG. 20, the spine band 42 and shoulder bands 24 are illustrated to describe the location of the inner layer 84 in accordance with some embodiments. However, it should be noted that the spine band 42 and shoulder bands 24 are located on the outer surface of the first garment portion, and not on the inner surface of the first garment portion. Alternatively, the spine band 42 and shoulder bands 24 can be located on both or either of the inner surface and the outer surface.

FIGS. 18-20 illustrate a sleeveless shirt (e.g., a tank top). However, the features described with respect to FIGS. 18-20 (e.g., the one or more pads 82 near the armholes and the inner layer 84) may be implemented in other types of garments, such as short or full/long sleeve shirts, bras, and bra tops.

FIGS. 21A-21C and 22 show a garment 90 in accordance with some embodiments. As explained above, many of the details of the embodiments described with respect to FIGS. 1-20 apply to the garment 90, and, therefore the description of these details is not repeated for brevity.

Figure 21A:
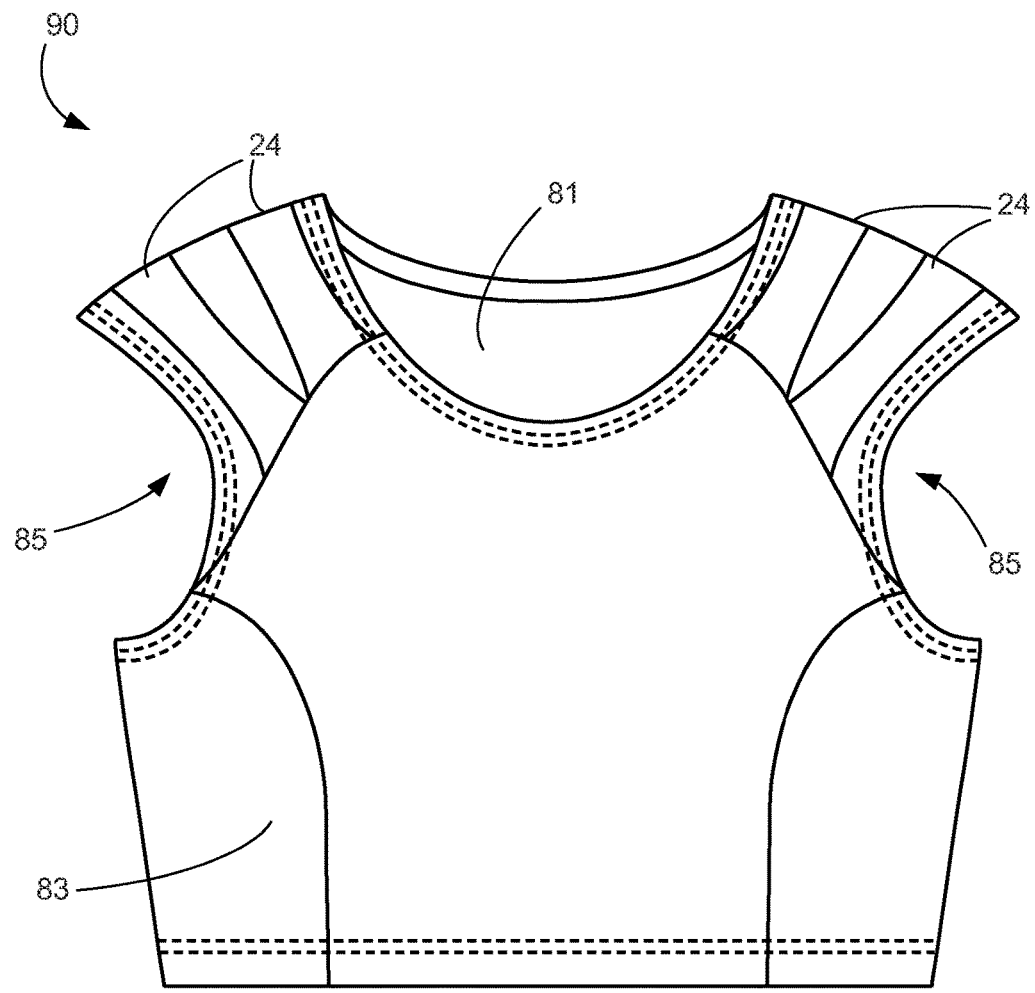
FIGS. 21A-21C are front elevational views of a garment in accordance with some embodiments.

FIG. 21A is a front elevational view of a garment 90 in accordance with some embodiments. The garment 90 is a bra (e.g., a sports bra). The bra includes an anterior portion (shown in FIG. 21A) and a posterior portion (shown in FIG. 22). In some embodiments, the bra is fabricated from an elastomeric material.

Figure 21B:
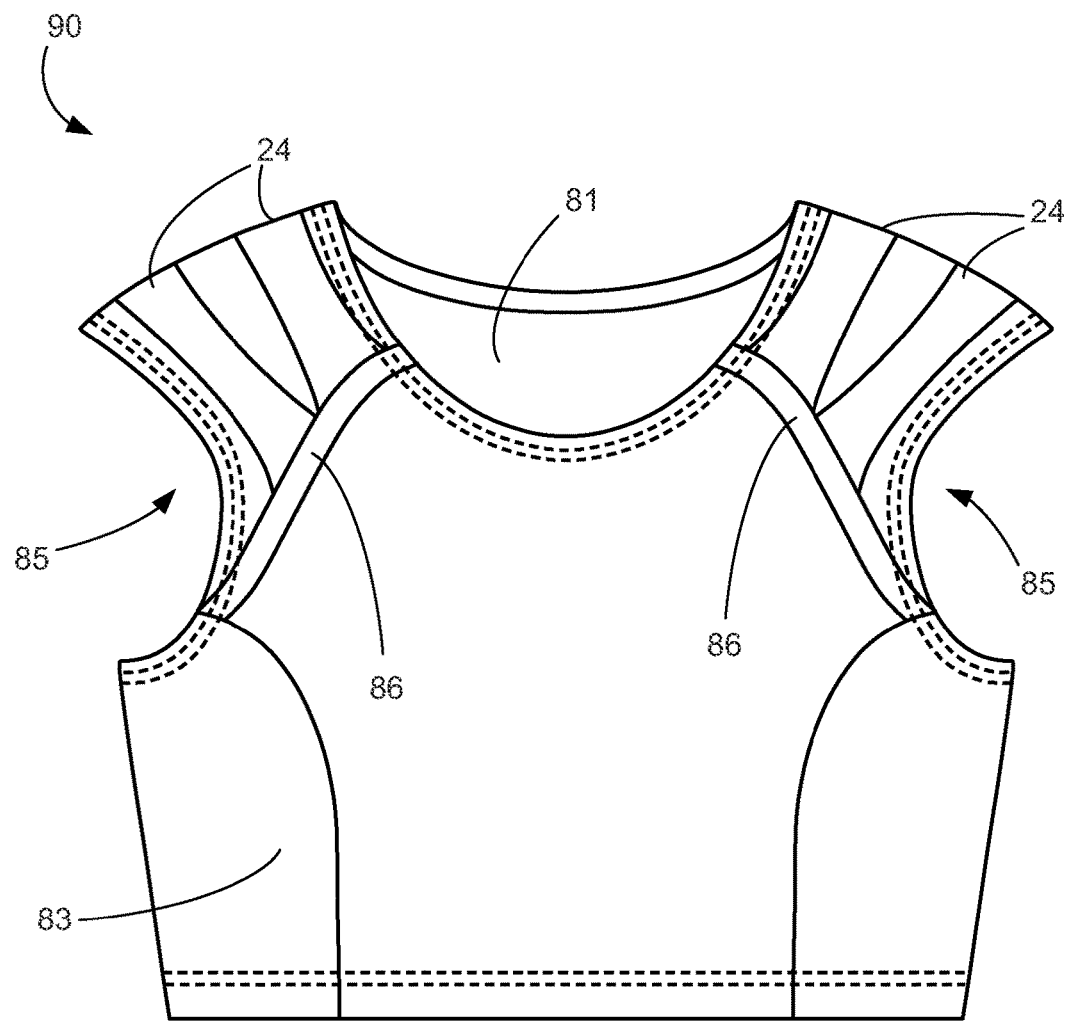

FIG. 21B is a front elevational view of the garment 90 in accordance with some other embodiments. The anterior portion of the bra includes one or more panel 86. In some embodiments, a respective panel 86 is made of a mesh (e.g., fabric with a plurality of openings). In some embodiments, the respective panel 86 is made of elastic fabric. In some embodiments, the respective panel 86 has a shape of a strip. In some embodiments, the respective panel 86 is diagonally positioned across an upper, front shoulder area of the anterior portion. In some embodiments, the respective panel 86 is placed at approximately two inches below each corocoid process located at front of each shoulder. This location of the respective panel 86 typically corresponds to a location where a short head of biceps and pectoralis minor attach respectively. This area is known to contain a high concentration of nerve receptors as well as acupuncture points and meridians. Biceps and pectoralis minor help control the forward and backward movement of the scapulae. The quality of the movement of the scapulae is a key to spinal and shoulder health and function. Stimulating the nerve receptors in this area improves the spinal and shoulder health and function. In some embodiments, the panel 86 is placed at an approximately 45 degree angle (e.g., between 30 to 60 degrees, 40 to 50 degrees, etc.) slopping downward to a lateral side of the anterior portion. In some embodiments, the panel 86 keeps straps 24 from migrating out of position (in particular, when the wearer is active). In other words, the panel 86 reduces migration of the straps 24. In some embodiments, the panel 86 also improves sensory motor stimulation by other straps and/or panels. In other aspects, the front elevational view of the garment 90 shown in FIG. 21B is similar to the front elevational view of the garment 90 shown in FIG. 21A.

FIG. 21A is a front elevational view of the garment 90 in accordance with some other embodiments. The anterior portion of the garment 90 includes a zipper 87 with a slider 88. In some embodiments, the zipper 87 facilitates wearing and taking off the garment 90. In some embodiments, the zipper 87 allows the wearer to control the compression provided by the garment 90. In other aspects, the front elevational view of the garment 90 shown in FIG. 21C is similar to the front elevational view of the garment 90 shown in FIG. 21A.

Figure 21C:
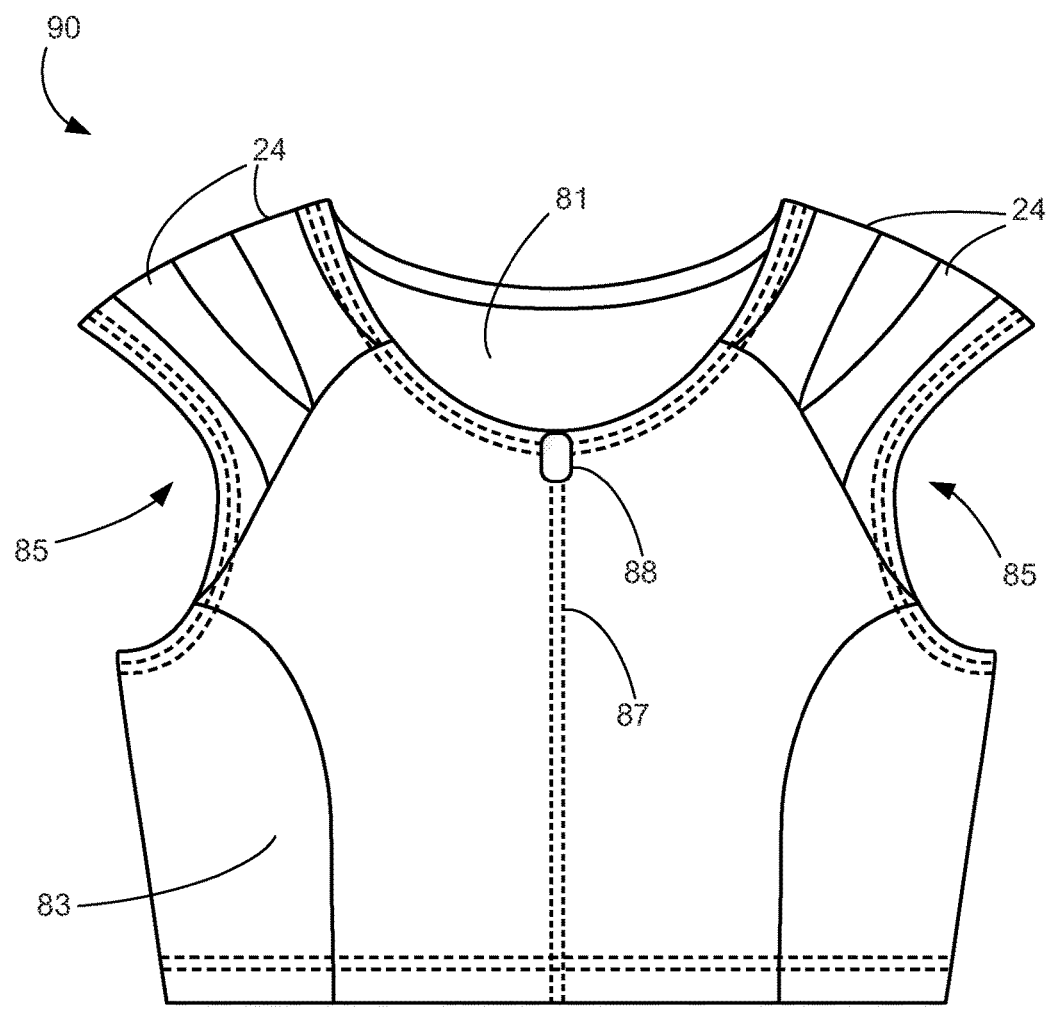
Figure 22:
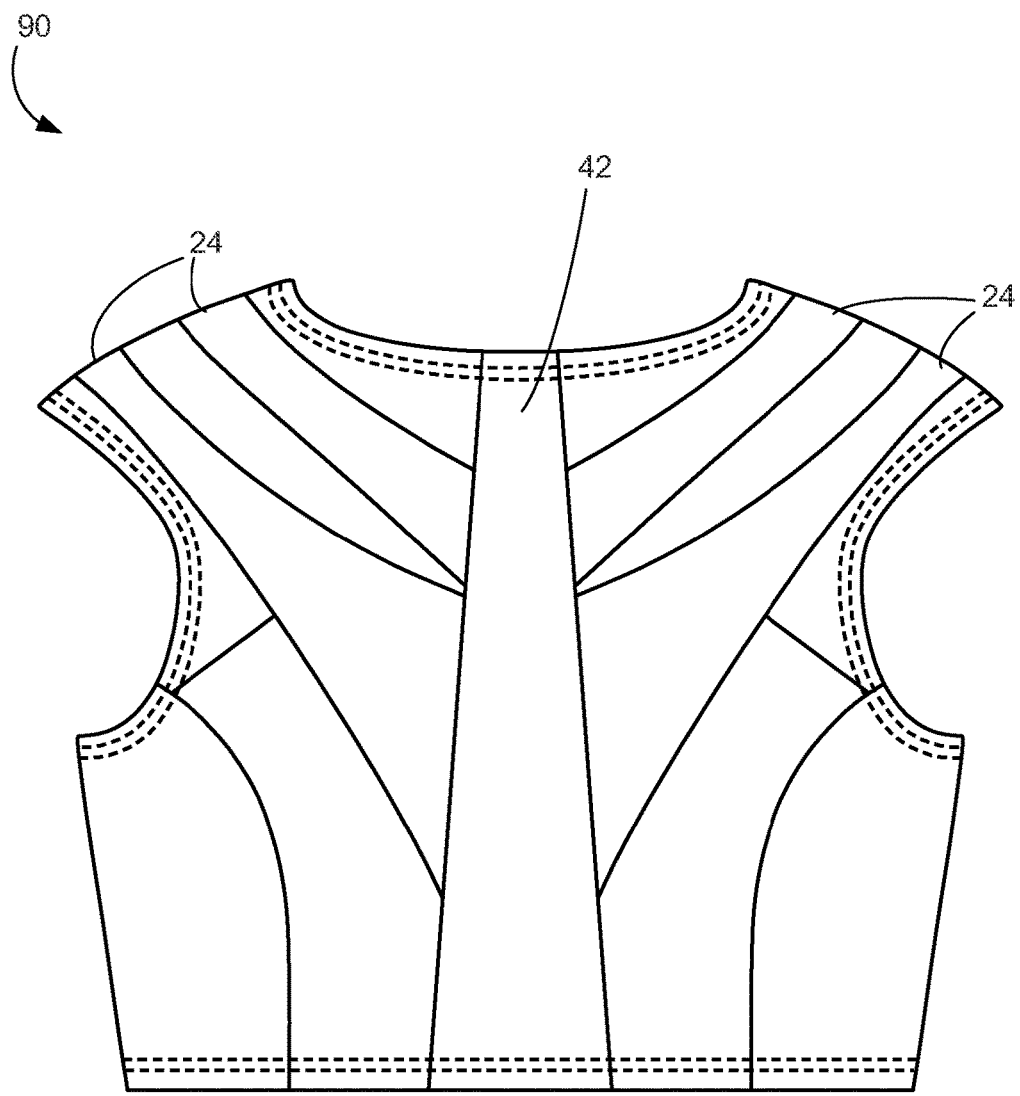
FIG. 22 is a rear elevational view of the garment of FIGS. 21A and 21C.

FIG. 22 is a rear elevational view of the garment 90 of FIGS. 21A-21C. Shown in FIG. 22 is a spine band 42 attached to the posterior portion of the bra and fabricated from an elastomeric material, which may be the same or different elastomeric material from the elastomeric material used for the bra. The spine band is a strip and extends longitudinally across the posterior portion of the bra from a neck region of the bra toward a waist portion of the bra. As used herein, the waist portion of the bra refers to a portion of the bra that is positioned, in use, toward a waist of a wearer. However, the waist portion of the bra need not contact the waist of the wearer. In use, the spine band is positioned over a spine of a wearer and stimulates cutaneous nerve receptors in a portion of a wearer's skin underneath the spine band.

In some embodiments, the garment 90 is configured to allow natural motion of the wearer, while providing a viscoelastic resistance in a longitudinal direction along the at least one additional band for training body muscles for proper posture through muscle memory.

In some embodiments, the at least one additional band (e.g., the bands 24) having a shape of a strip is attached to the bra and configured such that in use, the at least one additional band applies a corrective force along a longitudinal direction of the at least one additional band when the wearer is in a neutral posture, for training body muscles for proper posture through muscle memory.

Thus, the garment 90 may be used to reduce back pain caused by incorrect posture, which is often aggravated by weight distribution on the chest region.

FIGS. 23-24 show the garment 100 in accordance with some embodiments. FIG. 23 is a front elevational view of a garment 100 in accordance with some embodiments. The garment 100 is sometimes called a sports bra tank top or a tank with bra. The garment 100 similar to the garment 90 shown in FIGS. 21-22. However, the garment 100 differs from the garment 90 in that the garment 100 extends to the waist region of the wearer, whereas the garment 90 need not extend to the waist region of the wearer. The tank top includes an anterior portion (shown in FIG. 23) and a posterior portion (shown in FIG. 24). In some embodiments, the tank top is fabricated from an elastomeric material.

FIG. 24 is a rear elevational view of the garment 100 of FIG. 24. As shown in FIG. 24, the garment 100 includes the spine band 42. In some embodiments, the garment 100 also includes shoulder bands 24, which are described above with respect to the garment 90 (FIGS. 21-22).

Many of the details of the embodiments described with respect to FIGS. 1-22 apply to the garment 100. Therefore, these details are not repeated for brevity.

In some embodiments, one or more garments described herein include one or more zippers (e.g., the zipper 87 shown in FIG. 21C). In some embodiments, at least one of the one or more zippers is included in an anterior portion of a respective garment (e.g., the zipper 87 shown in FIG. 21C). In some embodiments, at least one of the one or more zippers is included in a posterior portion of the respective garment. In some embodiments, at least one of the one or more zippers includes a single slider (e.g., the slider 88 shown in FIG. 21C). In some embodiments, at least one of the one or more zippers includes a plurality of sliders (e.g., two sliders). In some embodiments, at least one of the one or more zippers includes one or more locking sliders. In some embodiments, when in use, a user may adjust the compression provided by a respective garment by moving a respective slider of a respective zipper. For example, a user, wearing a shirt, may partially open a zipper to decrease the compression provided by a shirt or bra, or further close the zipper to increase the compression provided by the shirt or bra. When the zipper has two sliders, the user may adjust respective sliders (e.g., top and bottom sliders) to independently adjust the compression provided on different parts of the user. For example, the user may close the top slider to increase the compression around the upper torso and partially open the bottom slider to decrease the compression around the lower torso.

In some embodiments, one or more garments described herein include sleeves. In some embodiments, one or more garments described herein include short sleeves. In some embodiments, one or more garments described herein include long sleeves. For example, the garment 80 shown in FIGS. 18-19 may include short sleeves or long sleeves. Similarly, the garment 90 shown in FIGS. 21A-21C and 22 and the garment 100 shown in FIGS. 23-24 may include short sleeves or long sleeves. All other garments described herein (e.g., FIGS. 1-17) may include short sleeves or long sleeves.

In some embodiments, one or more garments described herein extend below the waist line of a user. In some embodiments, one or more garments described herein are configured to extend by a predefined length below the waist line of the user when in use. For example, one or more garments described herein are configured to extend approximately four inches (e.g., one to twelve inches, and more particularly, two to six inches) below the waist line of the user or the head of the user's femur. Generally, the extended length of the one or more garments increases the stimulation to muscles of the core (e.g., pelvic floor muscles, transversus abdominis muscles, internal oblique muscles, external oblique muscles, rectus abdominis muscles, etc.).

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A garment, comprising:
   a bra comprising an anterior portion and a posterior portion, the bra fabricated from an elastomeric material;
   a spine band attached to the posterior portion of the bra and fabricated from an elastomeric material, the spine band having a shape of a strip extending longitudinally across the posterior portion of the bra from a neck region of the bra toward a waist portion of the bra, such that in use, the spine band is positioned over a spine of a wearer; and
   at least one additional band attached to the bra and also fabricated from an elastomeric material, wherein the at least one additional band includes four or more shoulder bands, each shoulder band being a strip radiating from the spine band having the shape of a strip and extending over a respective shoulder region of the bra to the anterior portion of the bra and the strip of each shoulder band being directly connected to the spine band having the shape of a strip, and the four or more shoulder bands comprise at least two inner shoulder bands and at least two outer shoulder bands, the at least two inner shoulder bands being positioned between the at least two outer shoulder bands, the at least two inner shoulder bands being spaced apart from the at least two outer shoulder bands, wherein a portion of the bra located between an inner shoulder band and an outer shoulder band extending over the respective shoulder region of the bra is fabricated from an elastomeric material that is distinct from the elastomeric material from which the four or more shoulder bands are fabricated.

2. The garment of claim 1, wherein the bra defines an inner surface and an outer surface, at least a first portion of the inner surface being configured to contact the wearer, and the garment further comprises an inner layer attached to a second portion of the inner surface distinct from the first portion of the inner surface.

3. The garment of claim 2, wherein the inner layer is made from plastisol.

4. The garment of claim 2, wherein the inner layer is made from silicone.

5. The garment of claim 2, wherein the inner layer is formed by spraying plastisol on the inner surface of the bra.

6. The garment of claim 2, wherein the inner layer has a trapezoidal shape.

7. The garment of claim 2, wherein the inner layer is configured to contact a scapular region of the wearer.

8. The garment of claim 1, wherein the four or more shoulder bands include inner shoulder bands and outer shoulder bands, where the inner shoulder bands are positioned between the outer shoulder bands.

9. The garment of claim 8, further comprising diagonal panels attached at least to the anterior portion of the bra, each diagonal panel having a shape of a strip sloping downward to a lateral side of the anterior portion, wherein the four or more shoulder bands are connected to the diagonal panels.

10. The garment of claim 1, wherein the bra defines an inner surface, an outer surface, and two arm holes, the inner surface being configured to contact the wearer; and the garment further comprises one or more pads attached to the bra adjacent to each arm hole, wherein the one or more pads are fabricated from an elastomeric material.

11. The garment of claim 1, wherein the bra is fabricated from a first elastomeric material, and the spine band and the at least one additional band are fabricated from a second elastomeric material that is different from the first elastomeric material.

12. The garment of claim 1, wherein the at least one additional band extends from the spine band.

13. The garment of claim 1, wherein the garment is configured to allow natural motion of the wearer, while providing a viscoelastic resistance in a longitudinal direction along the at least one additional band for training body muscles for proper posture through muscle memory.

14. The garment of claim 1, wherein the at least one additional band is attached to the bra and configured such that in use, the at least one additional band applies a corrective force along a longitudinal direction of the at least one additional band when the wearer is in a neutral posture, for training body muscles for proper posture through muscle memory.

15. The garment of claim 1, wherein the at least one additional band is attached to the bra, such that in use, the at least one additional band applies shear force toward a middle section of the spine band, on the wearer's skin underneath the at least one band.

16. The garment of claim 1, wherein a portion of the bra adjacent to the spine band is fabricated from a first elastomeric material, and the spine band is fabricated from a second elastomeric material that is different from the first elastomeric material.

17. The garment of claim 1, wherein the strip of each shoulder band is connected at one end to the spine band having the shape of a strip and at an opposite end to the anterior portion of the bra.

18. The garment of claim 1, wherein the strip of each shoulder band is connected only at one end to the spine band having the shape of a strip and at an opposite end to the anterior portion of the bra.

19. A method of stimulating a wearer's sensory motor system, comprising:
donning a garment that covers at least a portion of a wearer's torso, wherein the garment comprises:
a bra comprising an anterior portion and a posterior portion, the bra fabricated from an elastomeric material;
a spine band attached to the posterior portion of the bra and fabricated from an elastomeric material, the spine band having a shape of a strip extending longitudinally across the posterior portion of the bra from a neck region of the bra toward a waist portion of the bra along a region that is, in use, positioned over a spine of a wearer; and
at least one additional band attached to the bra and fabricated from an elastomeric material, wherein the at least one additional band includes four or more shoulder bands, each shoulder band being a strip radiating from the spine band having the shape of a strip and extending over a respective shoulder region of the bra to the anterior portion of the bra and the strip of each shoulder band being directly connected to the spine band having the shape of a strip, and the four or more shoulder bands comprise at least two inner shoulder bands and at least two outer shoulder bands, the at least two inner shoulder bands being positioned between the at least two outer shoulder bands, the at least two inner shoulder bands being spaced apart from the at least two outer shoulder bands, wherein a portion of the bra located between an inner shoulder band and an outer shoulder band extending over the respective shoulder region of the bra is fabricated from an elastomeric material that is distinct from the elastomeric material from which the four or more shoulder bands are fabricated;
moving while wearing the garment; and
stimulating the cutaneous nerve receptors in one or more portions of a wearer's skin underneath the at least one additional band by providing force along a longitudinal direction of the at least one additional band.

\* \* \* \* \*